(12) United States Patent
Martello

(10) Patent No.: US 12,383,241 B2
(45) Date of Patent: Aug. 12, 2025

(54) RELEASING STOPPER, CONTAINER PROVIDED WITH STOPPER AND KITS AND RELEASING METHOD ASSOCIATED THERETO

(71) Applicant: Copan Italia S.P.A., Brescia (IT)

(72) Inventor: Giorgio Martello, Brescia (IT)

(73) Assignee: Copan Italia S.p.A., Brescia (IT)

( * ) Notice: Subject to any disclaimer, the term of this patent is extended or adjusted under 35 U.S.C. 154(b) by 0 days.

(21) Appl. No.: 17/641,349

(22) PCT Filed: Sep. 10, 2020

(86) PCT No.: PCT/IB2020/058406
§ 371 (c)(1),
(2) Date: Mar. 8, 2022

(87) PCT Pub. No.: WO2021/048778
PCT Pub. Date: Mar. 18, 2021

(65) Prior Publication Data
US 2022/0338848 A1    Oct. 27, 2022

(30) Foreign Application Priority Data
Sep. 11, 2019  (IT) .................... 102019000016112

(51) Int. Cl.
*A61B 10/00* (2006.01)
*B01L 3/00* (2006.01)

(52) U.S. Cl.
CPC ........ *A61B 10/0096* (2013.01); *B01L 3/5029* (2013.01); *A61B 10/0045* (2013.01);
(Continued)

(58) Field of Classification Search
CPC ............ A61B 10/0096; A61B 10/0045; B01L 3/5029; B01L 2300/042; B01L 2300/047;
(Continued)

(56) References Cited

U.S. PATENT DOCUMENTS

| 4,720,017 A | 1/1988 | Pestes |
| 6,360,908 B1 | 3/2002 | Kline |

(Continued)

FOREIGN PATENT DOCUMENTS

| EP | 0520408 A3 | 12/1992 |
| EP | 3220832 A0 | 9/2017 |

(Continued)

OTHER PUBLICATIONS

International Search Report/Written Opinion, issued by European Patent Office on May 2, 2021; 17 pages.

(Continued)

*Primary Examiner* — Samuel P Siefke
(74) *Attorney, Agent, or Firm* — Fish & Richardson P.C.

(57) ABSTRACT

A releasing stopper for a container, the stopper including a first body configured to be directly coupled with the container and comprising a coupling element for allowing the removable fastening of the stopper on the container; a second body, axially movable with respect to the first body along a predefined axis of the stopper and cooperating with the first body for defining a reservoir at least temporarily insulated from the outer environment, a membrane or collapsible septum constituting at least a portion of the reservoir wall, openable and/or breakable for allowing the communication of the reservoir with the outer environment. The stopper includes a first closed configuration, wherein the reservoir is insulated from the outer environment, and a second open configuration, wherein the reservoir is in communication with the outer environment, and wherein the membrane or collapsible septum is opened by a perforation or opening element distinct from the stopper.

17 Claims, 9 Drawing Sheets

(52) U.S. Cl.
CPC ... *B01L 2300/042* (2013.01); *B01L 2300/047* (2013.01); *B01L 2300/0609* (2013.01); *B01L 2300/0672* (2013.01); *B01L 2400/0683* (2013.01)

(58) Field of Classification Search
CPC ..... B01L 2300/0609; B01L 2300/0672; B01L 2400/0683
See application file for complete search history.

(56) References Cited

U.S. PATENT DOCUMENTS

| | | | |
|---|---|---|---|
| 9,651,557 | B2 | 5/2017 | Jehuda-Cohen |
| 2004/0005246 | A1 | 1/2004 | Efthimiadis et al. |
| 2008/0272283 | A1* | 11/2008 | Feldsine ............... G01N 21/763 250/229 |
| 2013/0092690 | A1* | 4/2013 | Skakoon ............ B65D 51/2835 220/277 |
| 2015/0111767 | A1 | 4/2015 | Jehuda-Cohen |
| 2017/0001191 | A1 | 1/2017 | Biadillah et al. |
| 2019/0118172 | A1 | 4/2019 | Staton |
| 2019/0142395 | A1 | 5/2019 | Bartelucci |

FOREIGN PATENT DOCUMENTS

| | | |
|---|---|---|
| JP | S56-113430 | 9/1981 |
| JP | H05-187976 | 7/1993 |
| JP | 2011-107080 | 6/2011 |
| RU | 2204511 | 5/2003 |
| RU | 2220083 | 12/2003 |
| RU | 2240270 | 11/2004 |
| RU | 2692433 | 6/2019 |
| WO | WO 2000/007898 | 2/2000 |

OTHER PUBLICATIONS

Office Action in Russian Appln. No. 2022104111, mailed on Sep. 10, 2023, 72 pages (with English translation).
Office Action in Japanese Appln. No. 2022513308, mailed on Aug. 13, 2024, 8 pages (with English translation).

* cited by examiner

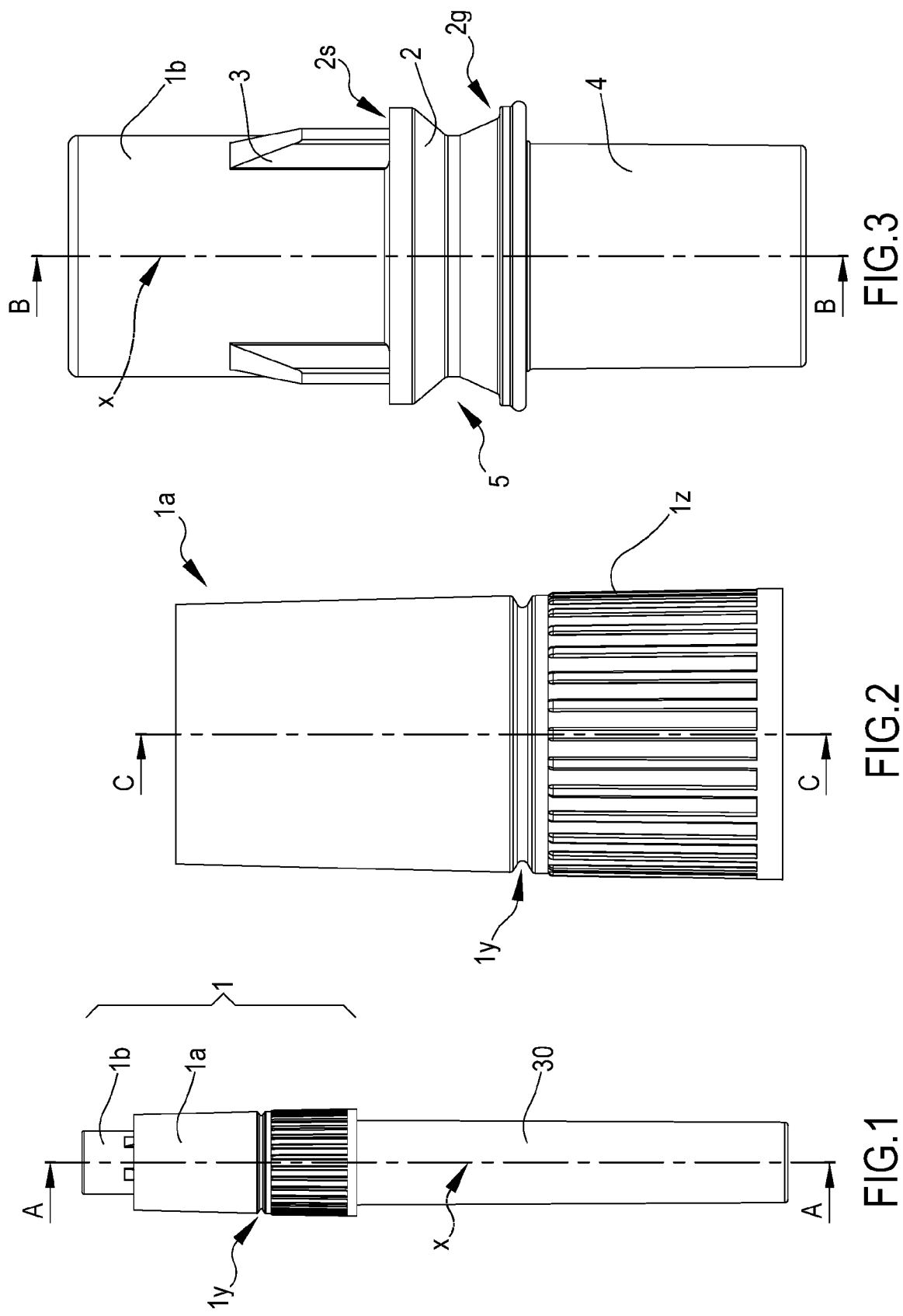

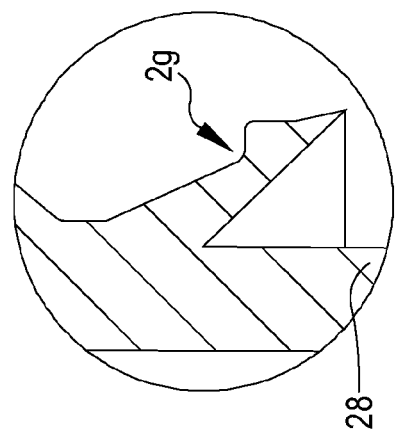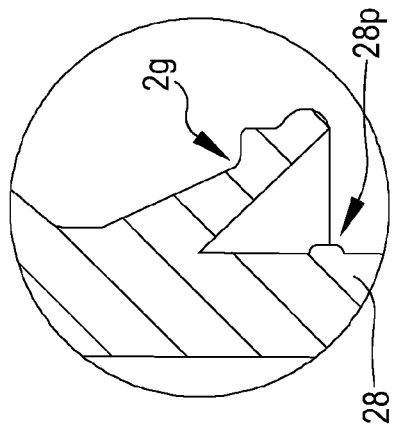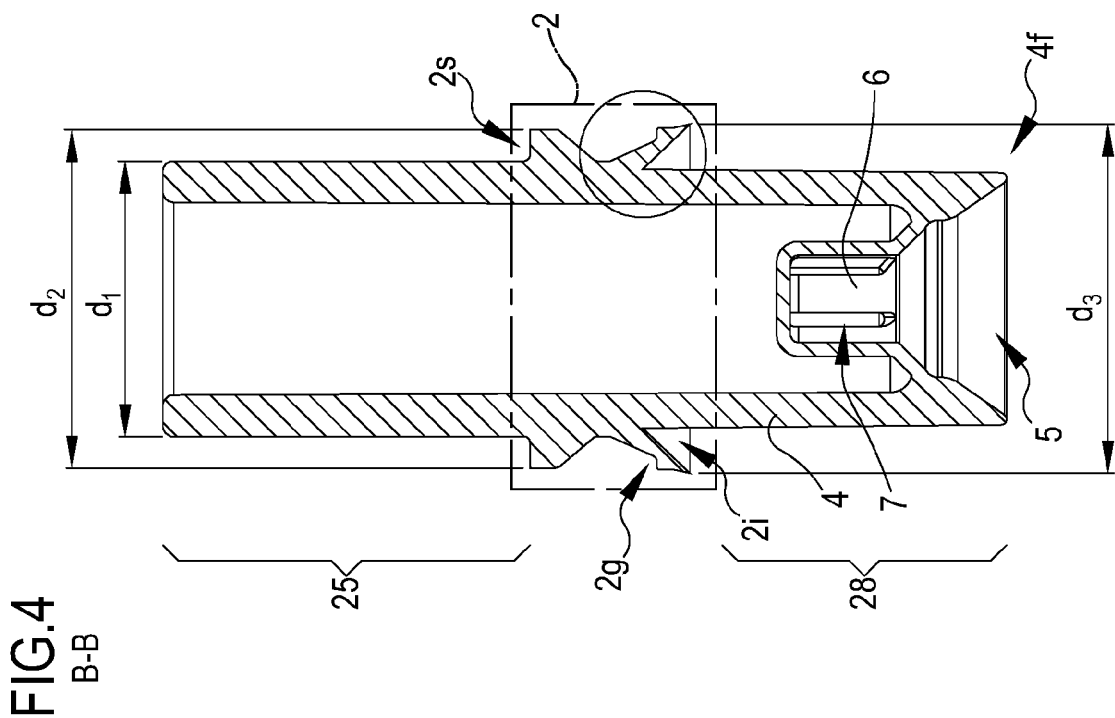

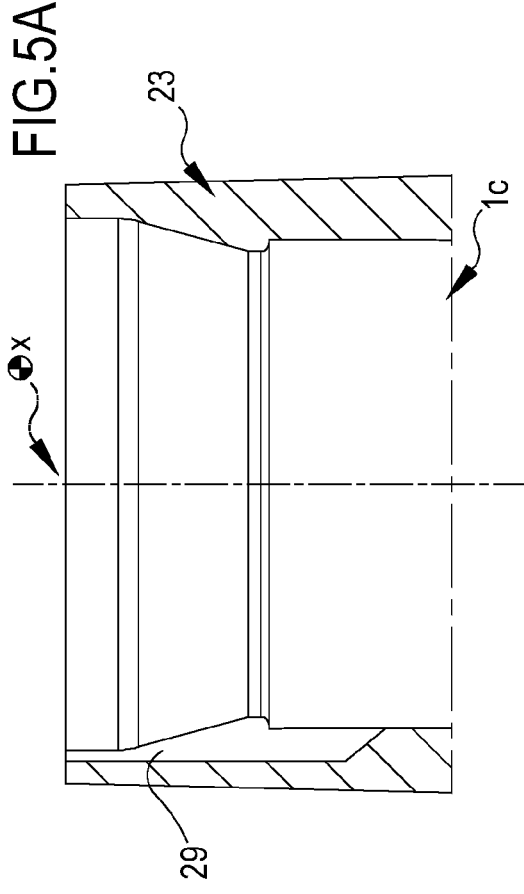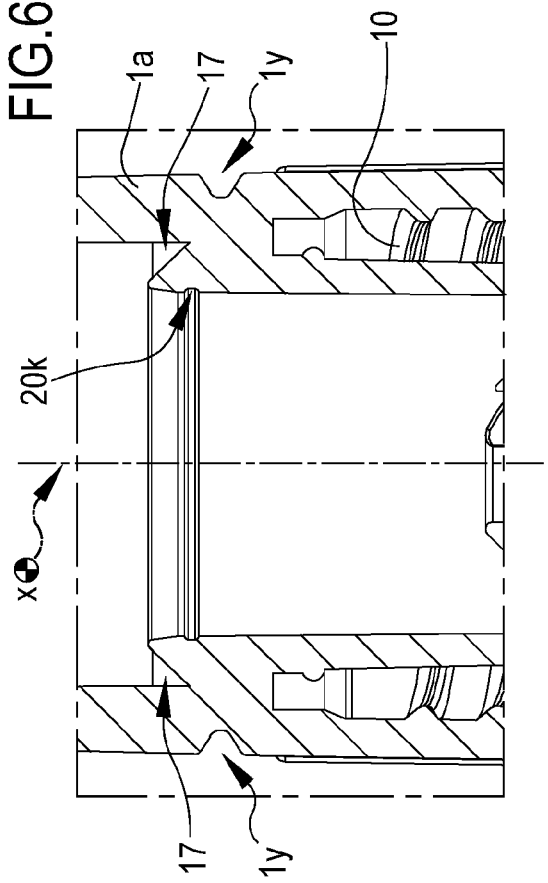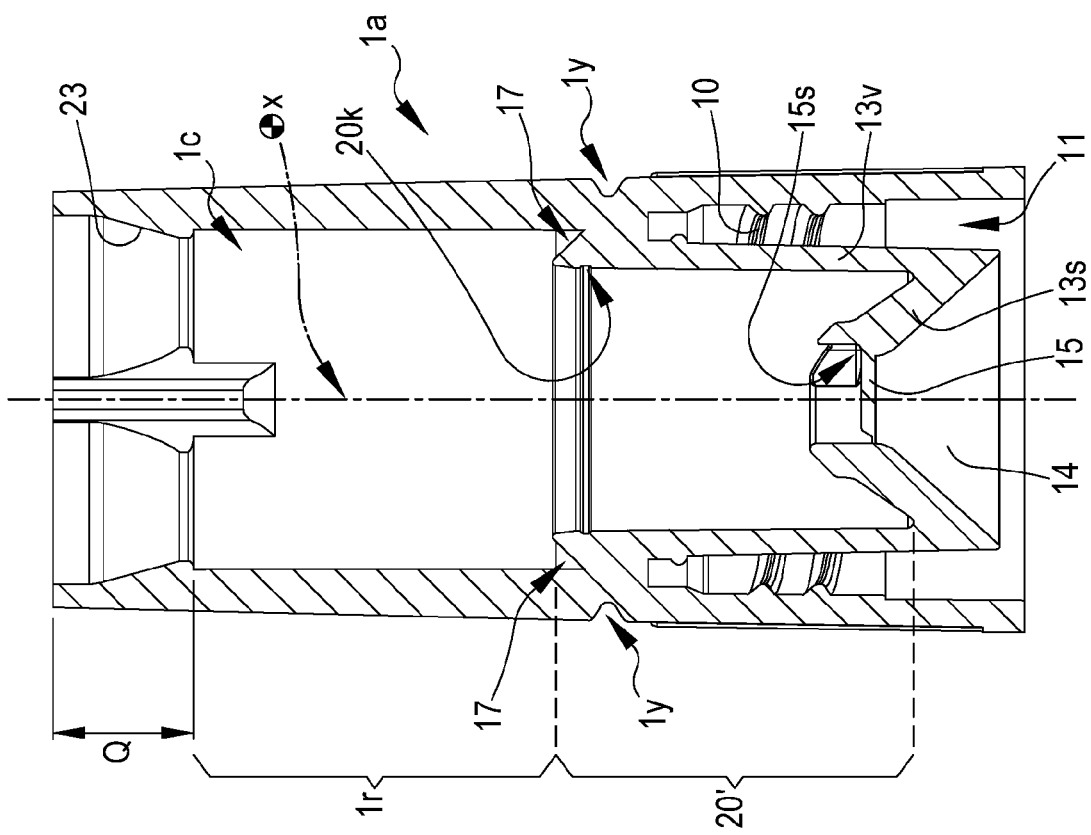

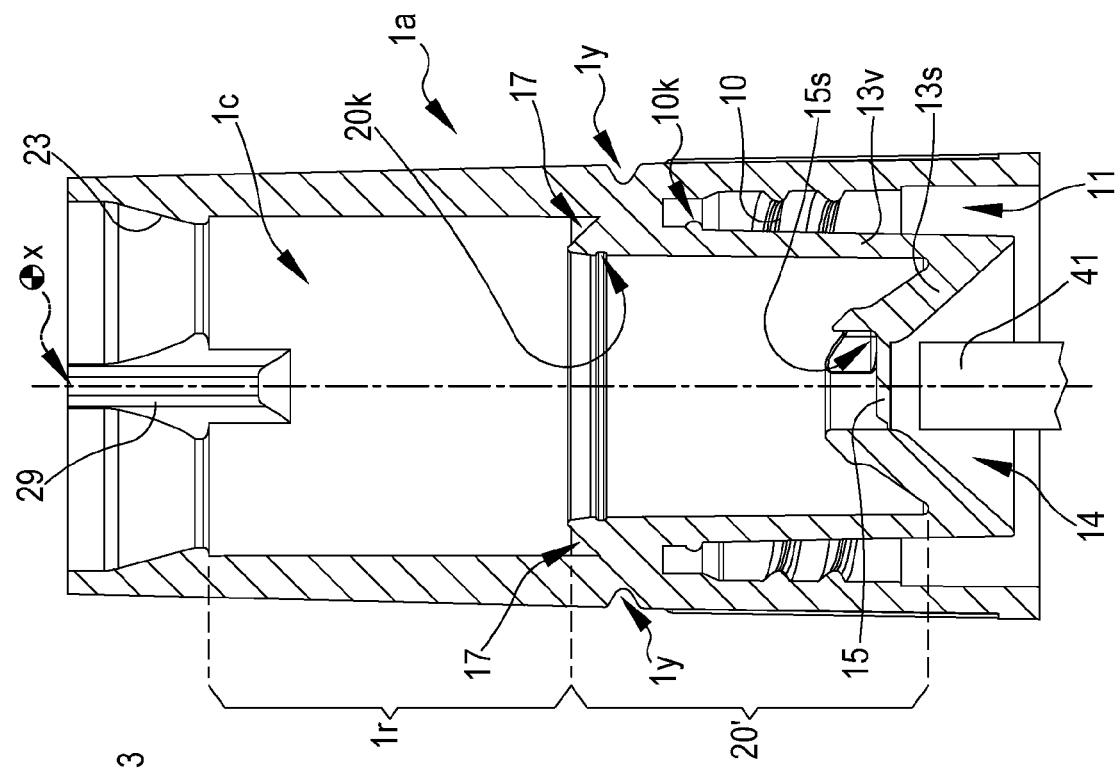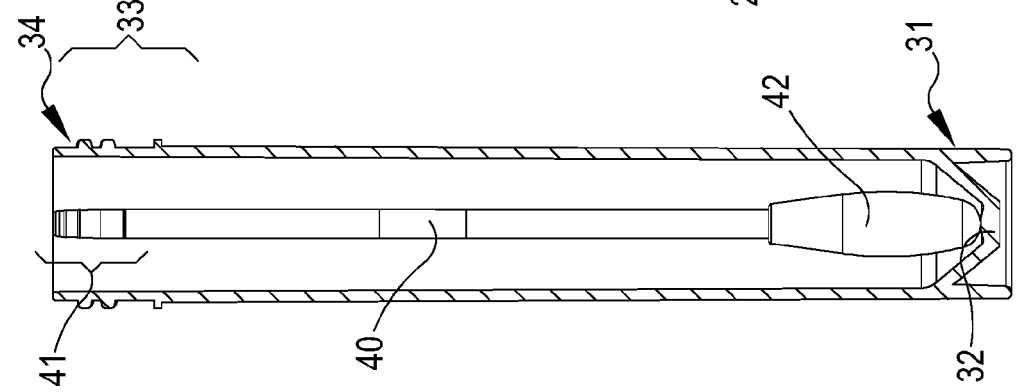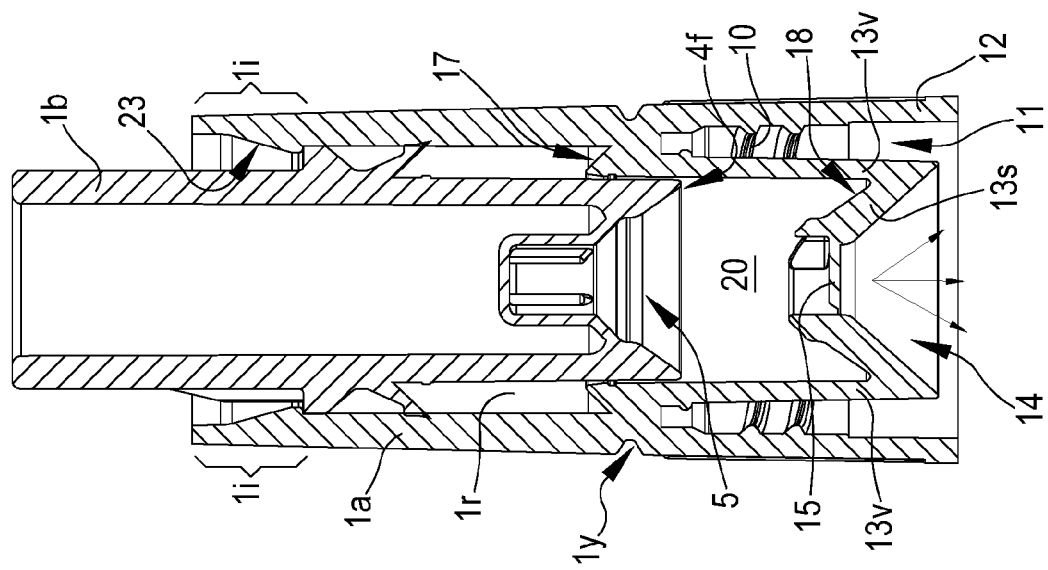

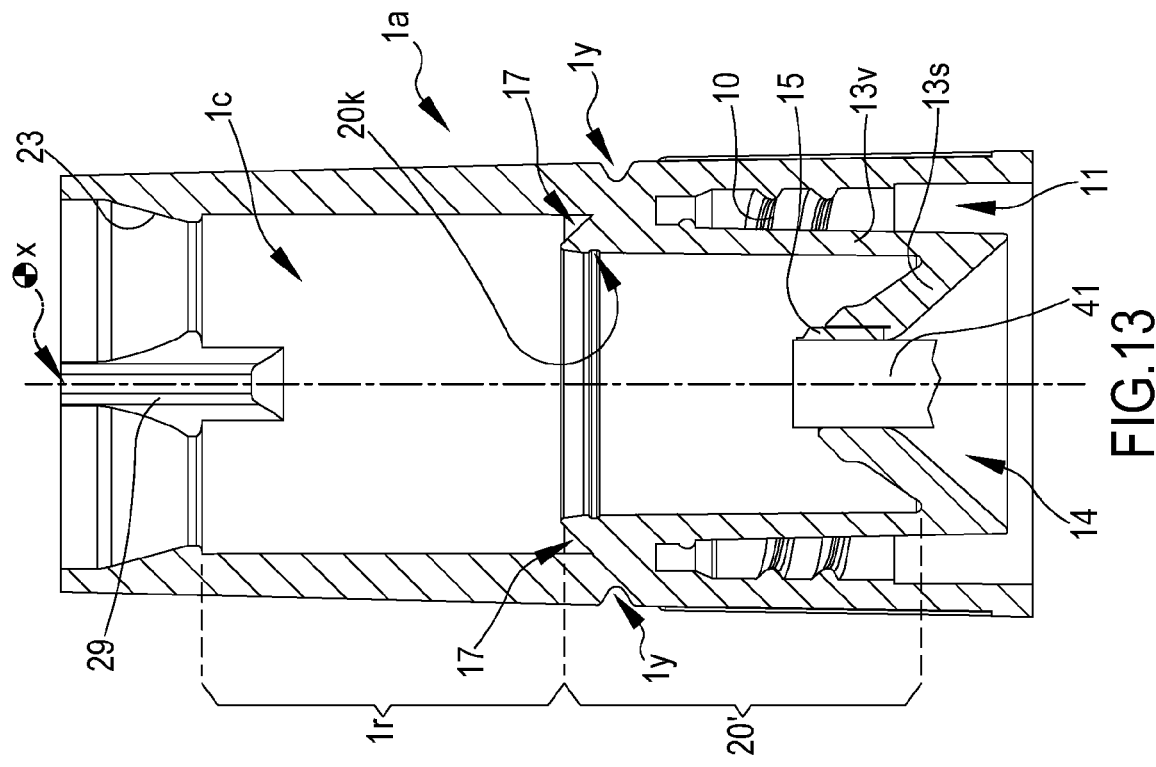
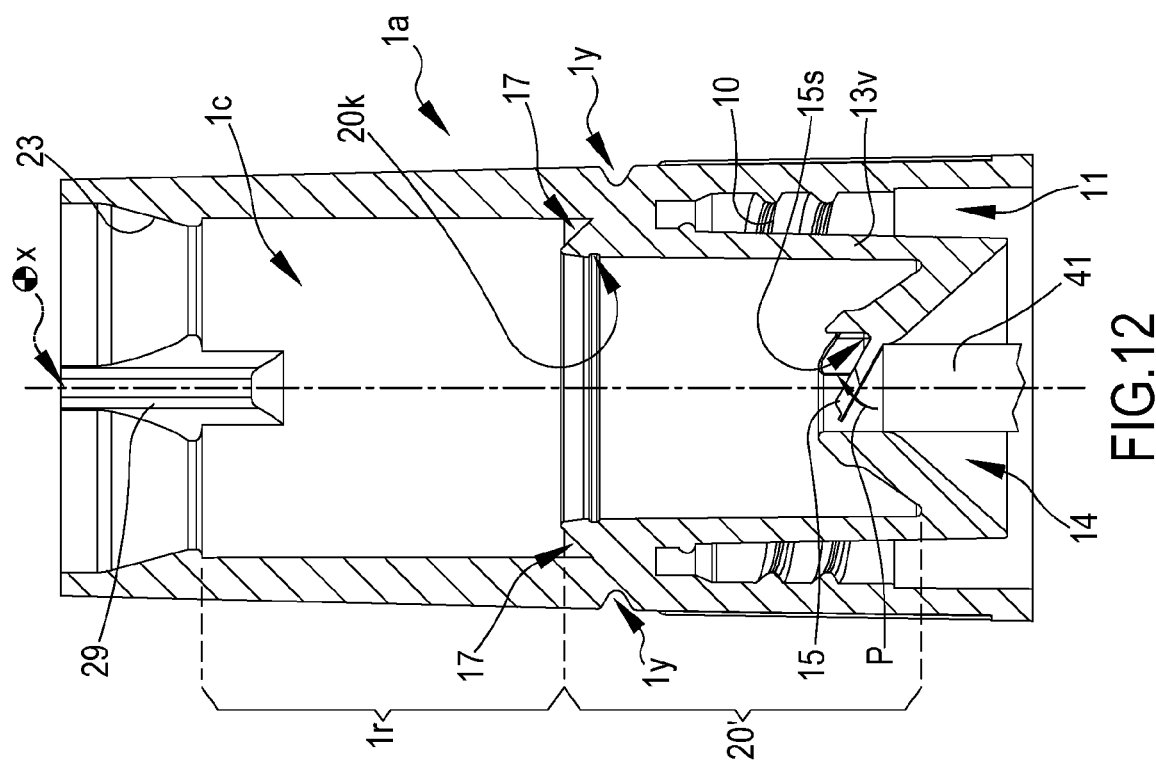

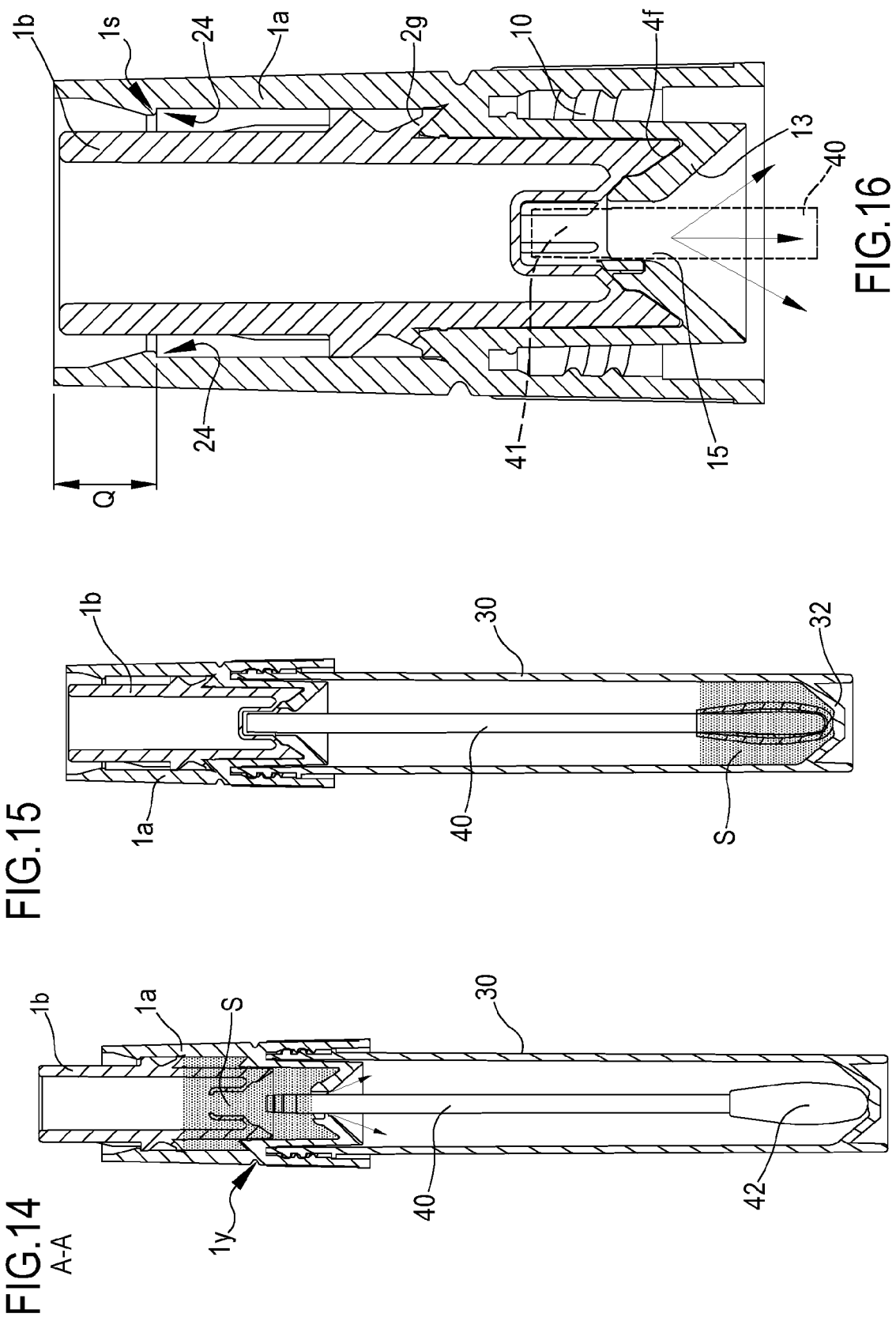

RELEASING STOPPER, CONTAINER PROVIDED WITH STOPPER AND KITS AND RELEASING METHOD ASSOCIATED THERETO

CROSS-REFERENCE TO RELATED APPLICATION(S)

This application is a U.S. National Phase Application under 35 U.S.C. § 371 and claims the benefit of priority to International Application Serial No. PCT/162020/058406, filed Sep. 10, 2020, which claims priority to Italian Application Serial No. 102019000016112, filed Sep. 11, 2019, the contents of which are hereby incorporated by reference.

TECHNICAL FIELD

The present disclosure refers to the field of closing elements for containers and in details relates to a releasing stopper. The present disclosure also refers to a container provided with the above-mentioned stopper, and also refers to a releasing method of a substance in the container.

STATE OF THE ART

The releasing stoppers are stoppers for containers suitable for storing substances in liquid or solid shape, for example in powdered shape, in order to release it in determined conditions, for example in a container to which the stopper is associated. The releasing stoppers of known type typically comprise a first operating configuration in which the substance is contained in a recess of defined volume in the stopper and a second operating configuration in which the recess is opened, allowing the release of the substance. Typically, the release of the substance takes place in the container in a configuration in which the stopper is constrained to the container.

Stoppers of known type can show a movable part, typically not the one directly connected to the container itself, which shows breaking elements suitable for opening a membrane which puts into communication the recess with the outer environment.

Such stoppers can be opened inadvertently and release the substance. The opening can take place either with the stopper opportunely fixed to the container or with a stopper free from the container. If the substance is harmful, or likely to degrade, the release of the substance out of the container can be dangerous or lead to degradation and consequent substantial non-usability of the substance.

It should be noted that releasing stoppers are often used not only by professional operators but also by private users, and can be handled by children.

In the field of collection and/or storage and/or analysis of biological and microbiological samples, it is known the use of test tubes or more generally of containers, closable by a stopper, within which containing biological samples, loose or deposited through a sampling element.

It is also known that samples of biological material can have to be subjected to treatment with reagents that can be poisonous or otherwise toxic.

In certain types of analysis, the use of the reagent must be subordinate to the use in a closed environment, i.e. with direct release within the container, for reasons of chemical reaction, degradation of the reagent, or for the safety of the operator. Nevertheless, certain reagents are very expensive, and their dispersion—in addition to the risk of causing the above-mentioned problems—can also involve a considerable expense.

From the US patent application 2013/0092690 is known a container for biological sample provided with a stopper suitable for containing an agent; the stopper has an ampoule and a perforation element that moves inside the stopper housing. If the stopper is handled badly, and in particular compressed along its longitudinal axis, the content of the ampoule could be inadvertently released, with consequent risk of exposure of the operator to danger and/or with the inevitable dispersion of the agent contained in the ampoule.

It should be noted that the present section is presented only in order to show some problems that the concepts herein are intended to address. The embodiments possibly described in this section should not be understood as part of the state of the art solely because they have been described here.

It has also been observed that many releasing stoppers are provided with structures comprising a large quantity of separate parts, provided each other with sealing rings, which contribute to cause a constructive and mounting complexity of the stopper itself. These sealing rings are in particular made of silicone or rubbery material that with time can lose its plastic deformability capacities, with the consequent risk of leakage of the substance contained in the stopper. In addition, this silicone or rubbery material could be not chemically compatible or otherwise react with some substances or reagents present in the reservoir of the stopper. The Applicant has in fact observed that stoppers containing substances are often stored for long periods, even longer than a year.

The purpose of the present disclosure is to describe a releasing stopper, a container for that stopper, as well as a kit comprising the container, the stopper and an element for the collection of biological samples that will help to solve the above described drawbacks.

Summary Section

The objects of the present disclosure are now described with reference to some aspects aimed at describing the main characteristics of the concepts herein. The aspects here described can be combined with each other, in alternative and/or cumulative combination, and/or with portions of the detailed description or related claims.

According to an aspect it is described a releasing stopper (1), suitable for and/or intended to be removably coupled with a container (30) and configured to contain and selectively release a substance (S) in the container (30), the stopper (1) comprising:

a first body (1a) configured to be directly coupled with the container (30) and comprising a coupling element (10) suitable for allowing the removable fastening of the stopper (1) in correspondence of an opening of the container (30) defining a first mounting configuration of the stopper on the container wherein, preferably, the stopper closes the container;

a second body (1b), coupled and movable with respect to the first body (1a) preferably axially and translably movable along a predefined axis (X) of the stopper (1) and defining with the first body (1a) at least one reservoir (20) configured to contain the substance (S), the reservoir (20) being insulated from the outer environment in at least a first closed configuration of the stopper, a closing element (15), constituting at least a portion of the reservoir wall (20) and facing the inside of the container (30) in the mounting configuration, the closing element (15) being configured to be selectively openable and/or breakable, defining at least a second open configuration of the stopper, through the action of a perforation or opening element (40, 41, 42) different from the stopper (1) and housed within the container, to make the reservoir (20) be in communication with the inside of the container (30).

According to another non-limiting aspect, the stopper comprises:
a first closed configuration, in which said reservoir (20) is insulated from the outer environment, and
a second open configuration, in which said reservoir (20) is in communication with the outer environment,
and wherein said membrane (15) or collapsible septum is configured to be opened by a perforation or opening element (40, 41, 42) distinct from said stopper (1).

According to the present disclosure, "breakable" means a closing element (15) of which a portion can be fractured so that its integrity can no longer be restored, and/or wherein it is no longer possible to restore the first closed configuration of the stopper.

According to another non-limiting aspect, the closing element (15) comprises or is a membrane or collapsible septum, and is optionally provided with a weakening portion.

According to another non-limiting aspect, the closing element (15) is positioned on the first body (1a) and/or is integral to the first body (1a) and/or, at least when the stopper is in the first closed configuration, the closing element (15) is integral to the first body (1a).

According to another non-limiting aspect, the closing element (15) is a waterproof element, configured and specifically designed to retain solids, in particular powders, liquids and/or gases.

According to another non-limiting aspect, at least a lower portion (28) of the second body is movably housed inside the first body, to define the reservoir (20).

According to another non-limiting aspect, the stopper comprises a tapered portion or element (14), optionally positioned on the first body (1a) suitable for facilitating the targeting and/or driving of at least part of the perforation element (40, 41, 42) towards the closing element (15), wherein the tapered portion (14) is positioned in a position which is longitudinally outer with respect to the membrane (15) and/or faces toward the closing element (15).

According to another non-limiting aspect, the closing element (15) is configured to be selectively openable and/or breakable, defining at least the second open configuration of the stopper, through the action of a perforation or opening element (40, 41, 42) different from the stopper (1) and different from the container and/or movably, optionally removably, housed inside the container.

According to another non-limiting aspect, the stopper (1) is a stopper for containers (30) of biological materials.

According to another non-limiting aspect, the stopper (1) is a stopper made of opaque material.

According to another non-limiting aspect, the second body (1b) comprises a cavity (6) configured to allow the removable engagement of an ending portion of the perforation or opening element (40, 41, 42), in particular for the removable engagement of an ending portion of the perforation or opening element (40, 41, 42) through introduction by contrast; the stopper being configured to allow the introduction by contrast only when in open configuration, in particular in substantial proximity or correspondence of the configuration of minimum axial extension.

According to another non-limiting aspect, the reservoir (20) is confined between the first body (1a), in particular at least by a lateral wall of the first body (1a), and the second body (1b), in particular a lower portion (28) of the second body (1b), more in particular being centrally limited by the lower portion (28) of the first body and/or wherein the lower portion (28) of the second body (1b) is introduced at least partially inside the reservoir (20).

According to another non-limiting aspect, the tapered portion or element (14) is integral to the first body (1a) and is substantially funnel-shaped, and is configured to be accessible from the inside of the container (30) and/or when the stopper is installed on said container.

According to another non-limiting aspect, the closing element is configured to withstand the pressure induced on the reservoir (20) by an axial compression of the second body (1b) with respect to the first body (1a), optionally manually induced by an operator; the closing element comprising a weakening portion suitable for breaking first by mechanical contrast induced by the perforation or opening element (40, 41, 42).

According to another non-limiting aspect, in said open configuration the substance (S) is at least partially released inside the container (30) and/or wherein the stopper is configured to release the substance (S) into the container (30) when in the open configuration, in particular by keeping, when coupled to the container (30), an insulation of the volume overall identified by the container (30)—reservoir (20) assembly insulated from the outer environment and/or in particular by causing an exclusive release of the substance through the opening identified by the breaking of the membrane (15).

According to another non-limiting aspect, the stopper comprises a retaining element of the closing element, configured to prevent the release and/or fall of the closing element (15) within the container (30); the retaining element being in particular configured to retain the closing element (15) inside the first body (1a).

According to another non-limiting aspect, the retaining element comprises a shoulder (15s) against which the closing element (15) rests or folds when in contrast with the perforation or opening element (40, 41, 42).

According to another non-limiting aspect, the shoulder (15s) is positioned in substantial correspondence of a channel between the reservoir (20) and the closing element (15) itself.

According to another non-limiting aspect, in the open operating configuration, the closing element (15) is retained by the shoulder (15s) and is trapped between the channel and part of the perforation or opening element (40, 41, 42) positioned within the channel.

According to another non-limiting aspect, in said open operating configuration, the membrane (15) is retained by the shoulder (15s) and is trapped between the channel and part of the perforation or opening element (40, 41, 42) positioned within the channel.

According to another non-limiting aspect, the closing element (15) is configured to break without releasing chips or portions.

According to another non-limiting aspect, the membrane (15) is rigid or substantially rigid.

According to another non-limiting aspect,
the second body (1b) is movable with respect to the first body (1a) and defines through its axial movement at least a configuration of maximum axial extension of the stopper (1) along a longitudinal axis (X) and a configuration of minimum axial extension of the stopper (1) along the longitudinal axis (X);

the first closed configuration comprises the maximum axial extension configuration and the second open configuration comprises the minimum axial extension configuration;

the second open configuration takes place in correspondence of a longitudinal extension, optionally substantially intermediate, between the longitudinal extension corresponding to the configuration of maximum extension and the longitudinal extension corresponding to the configuration of minimum longitudinal extension.

According to another non-limiting aspect, the first body (1a) comprises an upper cavity (1c), laterally delimited by a lateral wall, and a lower cavity separated each other by the presence of the closing element (15).

According to another non-limiting aspect, the stopper (1) is suitable for and/or destined to be removably coupled against a head portion of the container (30), and/or the first body (1a) is configured and destined to be removably coupled against a head portion of the container (30).

According to another non-limiting aspect, the first body (1a) is configured to be rigidly joined and/or fixed on a head portion of the container (30) and/or is configured to strike against a head portion of the container (30).

According to another non-limiting aspect, the second body (1b) is configured to be installed in correspondence of the upper cavity (1c) of said first body (1a).

According to another non-limiting aspect, the second body (1b) comprises an intermediate section comprising a sealing and linear translation limitation element (2), configured to determine a confinement of the reservoir (20) volume and to limit the stroke of the second body (1b) with respect to the first body (1a) between the configuration of maximum linear extension and the configuration of minimum linear extension of the stopper.

According to another non-limiting aspect, the second body comprises an upper portion (25) and a lower portion (28) with respect to which the intermediate section is longitudinally interposed.

According to another non-limiting aspect, the diameter substantially identified by the radially outermost section of the sealing element (2) is significantly greater than the diameter identified by the upper portion (25) and/or the lower portion (28) of the second body (1b).

According to another non-limiting aspect, the sealing element (2) comprises, optionally at a first upper height, a shoulder (2s) configured to engage in use with a retention portion (23) prominent from the inner face of the lateral wall of the first body (1a), the engagement between the retention portion (23) and the shoulder (2s) being such as to determine the impossibility of complete extraction of the second body (1b) from the first body (1a) when the latter has been previously inserted.

According to another non-limiting aspect, the sealing element (2) comprises a delimiting wall (2g) specifically configured to determine the sealing and confinement of the reservoir volume (20), the delimiting wall having a conformation such as to also determine the limitation of the translation of the second body (1b) with respect to the first body (1a) in the configuration of minimum axial extension.

According to another non-limiting aspect, the delimiting wall (2g) presents a radially outer portion developing on a circular profile—defined along a section orthogonal to said longitudinal axis (X)—and, optionally, comprises a radially outer portion with rounded profile.

According to another non-limiting aspect, the inner face of the side wall of the first body (1a) presents an undercut (17) positioned within the upper cavity and wherein the delimiting wall (2g) presents a portion configured to introduce itself into said undercut (17).

According to another non-limiting aspect, the above-mentioned portion presents a shape following the one of the undercuts.

According to another non-limiting aspect, the first body (1a) comprises an annular recess, optionally positioned at a substantially intermediate height between a minimum and a maximum height defined by the first body (1a) and/or positioned at a height substantially corresponding to the height at which the closing element (15) is located; the annular recess being configured to speed up the cooling of the first body (1a), in particular of the portion of the first body (1a) in correspondence of which it is positioned with respect to ending portions of the first body (1a).

According to another non-limiting aspect, the first body (1a) comprises a pressure release element (29), configured to allow the evacuation of a predefined volume of air when the second body (1b) is introduced into the first body (1a).

According to another non-limiting aspect, the pressure release element (29) is configured to allow the evacuation of a predefined volume of air when the second body (1b) is introduced into the first body (1a) in a non-operational mounting configuration of the second body (1b) into the first body (1a), without affecting the tightness of the reservoir (20) itself when at least the maximum axial extension configuration is reached.

According to another non-limiting aspect, in the configuration of maximum axial extension, the delimiting wall (2g) is at a lower or more inner height with respect to the minimum or more inner height assumed by the pressure release element.

According to another non-limiting aspect, the pressure release element (29) comprises a notch positioned in correspondence of a head portion of the inner face of the lateral wall of the first body (1a) and/or positioned in correspondence of a head portion of the upper cavity (1C).

According to another non-limiting aspect, the stopper is realized in plastic material resistant to acids and/or corrosive substances and/or characterized by the fact that it is realized in biocompatible plastic material, which does not release substances when in contact with biological samples.

According to another non-limiting aspect, the stopper is realized in biodegradable material, in particular biodegradable plastic material.

According to another non-limiting aspect, the first body (1a) comprises a gripping portion provided with elements able to allow the friction with a hand or fingers of an operator.

According to another non-limiting aspect, the first body (1a) comprises a plurality of recesses or knurls arranged in particular along a direction sensibly parallel to the direction substantially identified by the longitudinal axis (X).

According to another non-limiting aspect, the second body (1b) has a recess (5), optionally bell-shaped, configured to couple with a bottom portion of the reservoir (20) and having a shape substantially following the shape identified by the bottom of said reservoir (20).

According to another non-limiting aspect, said recess (5) opens on a cavity (6) configured to allow the removable engagement of an ending portion of the perforation or opening element (40, 41, 42) through introduction by contrast; said stopper being configured to allow the introduction by contrast only when in open configuration, in particular in substantial proximity or correspondence of the configuration of minimum axial extension.

According to another non-limiting aspect, said cavity (5) opens on the cavity (6), the cavity (6) having a plurality of restraint ribs (7) of the perforation or opening element (40, 41, 42).

According to another non-limiting aspect, the cavity (6) is provided with ribs (7) radially extending towards the centre of the cavity itself and/or substantially aligned along an axis substantially coinciding with the longitudinal axis of the stopper (1), said ribs (7) being configured to exert a friction force at the insertion and extraction of part of the perforation or opening element (40, 41, 42) with respect to the cavity (6) and to assist the transfer of at least part of the substance (S) from the reservoir (20) to the outside.

According to another non-limiting aspect, the first body (1a) comprises a side wall provided, on one of its outer face, with a gripping portion (1z) optionally characterized by knurling and/or ribs configured to facilitate the friction of the users fingers at least at the coupling of the stopper here described on the container (30).

According to another non-limiting aspect, the gripping portion (1a) is positioned in a base or lower portion of the side wall.

According to another non-limiting aspect, the first body (1a) comprises a cooling facilitating portion, configured to equalize the cooling of the first body (1a) at the realization; optionally, the cooling facilitating portion is positioned substantially in an intermediate area of the first body (1a).

According to another non-limiting aspect, the cooling facilitating portion comprises an annular recess (1y), optionally extending for the entire perimeter of the side wall of the first body (1a).

According to another non-limiting aspect, the substance (S) comprises solid material, optionally in granular and/or powdered form, and/or liquid material, optionally gelatinous material and/or Newtonian and non-Newtonian fluids, and/or comprises aeriform material, optionally in gas and/or steam form.

According to another non-limiting aspect, the releasing stopper (1) is a disposable stopper.

According to another non-limiting aspect, the second body (1b) comprises at least one rib (3), preferably a plurality of ribs (3); said rib (3) being configured to contain and/or limit offsets of the second body (1b) with respect to the first body (1a), optionally to limit the possibility of inclination of an axis of the second body (1b) with respect to an axis of the first body (1a).

According to another non-limiting aspect, said at least one rib (3) is positioned in an upper portion (25) of the second body (1b), and departs radially from the side wall of the upper portion (25), resulting—when the second body (1b) is introduced into the first body (1a)—in substantial contact with the inner face of a side wall of the first body (1a).

According to another non-limiting aspect, said lateral wall of the first body (1a) contributes to define a cavity within which the second body (1b) is introduced.

According to another non-limiting aspect, the at least one rib (3) is positioned upperly with respect to the intermediate section that comprises the sealing and linear translation limitation element (2).

According to another aspect, it is described a kit comprising:
 a container (30), configured to be closed by a releasing stopper (1),
 an element (40, 41, 42) for the collection and storage of a biological sample, suitable for realizing a perforation or opening element for the releasing stopper (1),
 a releasing stopper (1), suitable for being removably coupled with the container (30) and configured to contain and release a substance (S) in the container (30), the releasing stopper (1) being a stopper suitable and/or intended to be removably fastening of the container (30) and configured to contain and selectively release a substance (S) in the container (30), the stopper (1) comprising:
 a first body (1a) configured to be directly coupled with the container (30) and comprising a coupling element (10) suitable for allowing the removable fastening of the stopper (1) in correspondence of an opening of the container (30) defining a first mounting configuration of the stopper on the container wherein, preferably, the stopper closes the container;
 a second body (1b), coupled and movable with respect to the first body (1a), preferably axially and translably movable along a predefined axis (X) of the stopper (1), and defining with the first body (1a) at least a reservoir (20) configured to contain the substance (S), the reservoir (20) being insulated from the outer environment in at least a first closed configuration of the stopper,
 a closing element (15), constituting at least a portion of the reservoir wall (20) and facing inward the container (30) in the mounting configuration, the closing element (15) being configured to be selectively openable and/or breakable, defining at least a second open configuration of the stopper, through the action of a perforation or opening element (40, 41, 42) different from the stopper (1) and housed inside the container, to put the reservoir (20) in communication with the inside of the container (30).

According to another non-limiting aspect, the perforation or opening element (40, 41, 42) comprises a rod (40) and in the kit there is a dimensional ratio, in particular a difference, between a longitudinal development of the container (30) and a longitudinal development of the rod (40), in particular a difference of longitudinal development along an axis (X) of the axial extension of the container (30) along the said axis (X) with respect to the axial extension of the rod (40) along the same axis; the longitudinal development of the rod (40), in relation to the longitudinal development of the container (30) being such that, when the rod (40) is introduced into the container (30), it can interfere with the closing element (15) so that it can open or fracture it.

According to another non-limiting aspect, the rod (40) has a longitudinal development such that, when positioned inside the container (30), it protrudes out of the shape defined by the container itself.

According to another aspect, it is described a container (30) for the storage of a biological sample, said container comprising a body openable at least in correspondence of at least one own first portion (33) and provided with a lateral wall and a bottom wall (32) coupled to the lateral wall (30), said container (30) being configured to be removably coupled with a stopper (1) according to one or more of the previous aspects, such as to realize the perforation or opening element (40, 41, 42).

According to another non-limiting aspect, the container comprises an element (40, 41, 42) for the collection and/or storage of biological samples, provided with a rod (40) and a swab (42), optionally a flocked swab, to which the rod (40) is rigidly attached.

According to another non-limiting aspect, the container has a longitudinal development such that an ending portion (41) of the rod opposite to the portion in correspondence of which the swab (42) is located after the removable coupling of the stopper (1) on the container (30) determines a perforation of the closing element (15) and a partial introduction of the ending portion (41) of the rod (40) within the first body (1a).

According to another non-limiting aspect, the container comprises a substantially "V"-shaped bottom portion (32), optionally connected without interruption with the lateral wall of the container (30), wherein in correspondence of the bottom portion (32) the lateral wall progressively tapers towards the center of the container body (30); the bottom portion (32) being configured to exert a centering of the rod (40) and/or of the swab (42) for the collection of biological samples along the longitudinal axis (X) of the container (30). According to another non-limiting aspect, the bottom portion (32) cooperates with the guide portion (13s, 13v) of said stopper (1), and in particular with the second wall (13s), in order to contribute to the centring of the rod (40) along said longitudinal axis (X).

According to another non-limiting aspect, the container (30) is a container realized in plastic material, optionally realized in exclusively a single plastic material, optionally wherein the plastic material is biocompatible and/or does not release substances in contact with a biological sample.

According to another aspect it is described a method for the distribution of substances inside a releasing stopper according to one or more of the preceding aspects, and/or a kit according to one or more of the preceding aspects, the method comprising the following steps:

a step of positioning the substance within the first body (1a) of the stopper (1) so that the substance is deposited in the reservoir (20) delimited by the closing element (15);

a subsequent step of positioning of the second body (1b) at least partially within the first body (1a) so that through the positioning a confinement of the reservoir (20) and of the substance is caused within a closed volume, separated from the outer environment.

According to another non-limiting aspect, at least the step of positioning of the substance within the first body (1a) of the stopper and/or the subsequent step of positioning of the second body (1b) at least partially within the first body (1a) are steps performed automatically by a stopper assembling machine.

According to another non-limiting aspect, the method further comprises a step of coupling the stopper (1) with a container (30), wherein, as a result of the coupling, the container (30) is provided with a closed and limited volume, in correspondence of an opening thereof, by the presence of the stopper (1).

According to another non-limiting aspect, the method further comprises a step of pressure exerting on the second body (1b) of the stopper (1) after or in conjunction of which an axial compression of the stopper (1) is determined, which causes the progressive introduction of the second body (1b) within the first body (1a), the progressive introduction of the second body (1b) within the first body (1a) determining a corresponding progressive reduction of the volume of the reservoir (20) and a progressive distribution of the substance (S) within the container (30).

According to another aspect, it is therefore described a method for the distribution of substances within a container (30), in particular a container for samples of biological and/or microbiological material, through a releasing stopper according to one or more of the preceding aspects, said method comprising:

a step of coupling the stopper (1) with a container (30), wherein, as a result of the coupling, the container (30) is provided with a closed and limited volume, in correspondence of an opening thereof, by the presence of the stopper (1), a step of positioning of a perforation or opening element (40, 41, 42) inside the container (30), wherein due to the coupling of the stopper (1) with the container (30) and/or with the perforation or opening element (40, 41, 42) a perforation of the closing element (15) is determined, so that to put the inside of the container (30) in direct communication with the reservoir (20), a step of pressure exerting on the second body (1b) of the stopper (1) after or in conjunction of which an axial compression of the stopper (1) is determined, which causes the progressive introduction of the second body (1b) within the first body (1a), the progressive introduction of the second body (1b) within the first body (1a) determining a corresponding progressive reduction of the volume of the reservoir (20) and a progressive distribution of the substance within the container (30).

According to another non-limiting aspect, the perforation or opening or fracture of the closing element (15) determines at least a partial detachment of the closing element (15) from the first body (1a), of which the closing element (15) is integral part, at least before the perforation or opening or fracture.

According to another non-limiting aspect, due to the coupling of the stopper (1) with the perforation or opening element (40, 41, 42) a perforation or opening or fracture of the closing element (15) is determined, optionally a perforation or opening or fracture of a membrane (15) or collapsible septum of the stopper (1), such as to put in direct communication the inside of the container (30) with the reservoir (20).

According to another non-limiting aspect, the perforation or opening or fracture of the closing element (15) takes place before an engagement of the stopper (1) on the container (30) and/or before a direct coupling of the stopper (1) on the container (30).

According to another non-limiting aspect, the perforation of the closing element (15), in particular the membrane (15) or collapsible septum, takes place before a progressive screwing of the stopper (1) on the container (30).

According to another non-limiting aspect, due to the coupling of the stopper (1) with the container (30) a perforation of the membrane or collapsible septum is determined caused by an ending portion of the perforation or opening element (40, 41, 42) only when positioned within the container (30).

According to another non-limiting aspect, the coupling of the stopper (1) on the container (30) comprises a removable coupling of the first body (1a) of the stopper (1) on the container (30), in particular a removable coupling of the first body (1a) against a head portion of the container (30).

According to another non-limiting aspect, when the stopper (1) is coupled on the container (30), the first body (1a) is rigidly joined and/or is fixed to a head portion of the container (30) and/or strikes against a head portion of the container (30).

According to another non-limiting aspect, the removable coupling of the stopper (1) on the container (30) comprises a progressive screwing of the stopper (1), in particular the first body (1a) of the stopper (1) on the container (30).

According to another non-limiting aspect, the perforation or opening or fracture of the closing element (15) takes place following an engagement of the stopper (1) on the container (30) and/or following a direct coupling of the stopper (1) on the container (30), optionally following an axial compression of the assembly formed by the stopper (1) and the container (30), and/or following at least a partial screwing of the stopper (1) on the container (30).

According to another non-limiting aspect, the perforation of the closing element (15), in particular of the membrane (15) or collapsible septum, takes place by means of the progressive screwing of the stopper (1) on the container (30).

According to another non-limiting aspect, a completion of the progressive screwing of the stopper (1) on the container (30) determines the completion of the step of coupling of the stopper (1) with the container (30), and the container (30) is provided with a closed and limited volume, in correspondence of one of its openings, by the presence of the stopper (1).

According to another non-limiting aspect, following the perforation of the closing element (15), the ending portion (41) of the perforation or opening element (40, 41, 42) is introduced at least partially inside the first body (1a) and determines a retention of the closing element (15) on and/or within the first body (1a), in particular determining a trapping of the closing element (15) between itself, a lateral surface of a channel of substance (S) expulsion and a shoulder (15s) positioned in substantial correspondence of said expulsion channel.

According to another non-limiting aspect, the progressive axial compression of the stopper (1) ends in correspondence of a configuration of minimum axial extension of the stopper (1), wherein the second body (1b) is for a maximum part introduced within the first body (1a), optionally wherein the second body (1b) is totally introduced within the first body (1a); in said configuration of minimum axial extension the reservoir (20) being for maximum part, optionally substantially totally, emptied of the substance (S).

According to another non-limiting aspect, in correspondence of the configuration of minimum axial extension, the second body (1b) is in a position of block relatively to the first body (1a) such that axial extensions of the stopper (1) are operationally impossible; the position of block being determined by an engagement of a stopping ring (28p) of the second body (1b) in correspondence of a annular recess present in correspondence of an inner face of the lateral wall of the first body (1a).

According to another non-limiting aspect, the progressive axial compression of the stopper (1) determines a sliding of a flexible skirt (2g) of the second body (1b) on the inner face of the side wall of the first body (1a) in a direction substantially identified by the longitudinal axis (X) of the stopper, through which a seal of liquid and/or gas and/or powdered material is determined such as to force the leakage of at least part of the substance (S) only from the open channel through the breaking of the closing element (15).

According to another non-limiting aspect, with the axial compression, the sliding of the skirt (2g) takes place through an elastic deformation of the same after which a radially outer portion of said skirt (2g) exerts against the inner face of the lateral wall of the first body (1a) a force oriented substantially in orthogonal direction with respect to the direction of advancement of the second body (1b) within the first body (1a) induced by the axial compression itself.

According to another non-limiting aspect, the method comprises an irremovable engagement of an ending portion (41) of the perforation or opening element (40, 41, 42) in correspondence of a cavity (6) realized in correspondence of the second body (1b), said irremovable engagement happening as a result of the substantial axial compression of the stopper (1), and optionally happening in substantial correspondence or proximity of a configuration of minimal axial extension of the stopper (1).

According to another aspect, it is described the use of the stopper in accordance with one or more of the preceding aspects, for the use on containers configured and/or specifically intended to contain a biological and/or microbiological sample, and/or the use of the stopper in accordance with one or more of the preceding aspects for containing substances suitable for reacting and/or allowing the analysis of samples of biological and/or microbiological materials.

According to another aspect, it is described a machine for the assembly of a stopper 1 in accordance with one or more of the present aspects, the machine comprising manipulating elements configured at least to carry out an operation of positioning and/or pouring of a substance (S) within the first body (1a) of the stopper (1) so that the substance (S) is deposited in the reservoir (20) delimited by the closing element (15); the manipulating elements being also configured to carry out a subsequent operation of positioning of the second body (1b) at least partially within the first body (1a) so that through the positioning a confinement of the reservoir (20) and of the substance within a closed volume is determined, separated from the outer environment, the manipulating elements being configured to carry out the operation of positioning of the second body (1b) automatically, following the positioning and/or pouring of the substance (S) in the first body (1a).

According to another aspect, it is here described a releasing stopper (1), suitable for and/or intended to be coupled removably with a container (30) and configured to contain and selectively release a substance (S) in the container (30), wherein the stopper (1) comprises:
  a first body (1a) configured to be directly coupled with the container (30) and comprising a coupling element (10) suitable for allowing the removable fastening of the stopper (1) in correspondence of an opening of the container (30) defining a first mounting configuration of the stopper on the container wherein, preferably, the stopper closes the container;
  a closing element (15), constituting at least a portion of the reservoir wall (20) and facing the inside of the container (30) in the mounting configuration, the closing element (15) being configured to be selectively openable and/or breakable, defining at least a second open configuration of the stopper, through the action of a perforation or opening element (40, 41, 42) different from the stopper (1) and housed inside the container, to put the reservoir (20) in communication with the inside of the container (30); wherein
  the stopper comprises a closing indicator (10k), suitable for engaging on the container (30).

According to another non-limiting aspect, the closing indicator (10k) is configured and/or intended to create a contrast on the container (30) such as to contribute to the sealing of an inner cavity of the container (30).

According to another non-limiting aspect, the closing indicator (10k) is configured to allow the user to identify a configuration in which the stopper (1) is properly installed on the container (30) such as to complete the sealing and/or insulation of the inner cavity.

According to another non-limiting aspect, the closing indicator (10*k*) is suitable for engaging on or in correspondence of a closing counter-indicator (30*k*) placed on the container (30) determining a closing configuration of the container (30).

According to another non-limiting aspect, the closing indicator (10*k*) is suitable for engaging on or in correspondence of a closing counter-indicator (30*k*) positioned on the container (30) determining a configuration of complete closing of the container (30) and/or of sealing and/or complete delimitation of the inner volume of the container (30).

According to another non-limiting aspect, the closing indicator (10*k*) is an element protruding from a wall of the stopper (1), optionally a ring protruding from a wall of the stopper (1) and the closing counter-indicator (30*k*) comprises a recess, optionally an annular recess, positioned on the container (30).

According to another non-limiting aspect, the closing indicator (10*k*) is a recess positioned on a wall of the stopper (1), optionally an annular recess positioned on a wall of the stopper (1), and the closing counter-indicator (30*k*) comprises an element protruding from a wall of the container (30), optionally a ring protruding from a side of the container (30).

According to another aspect, it is described a kit comprising:
- a releasing stopper (1) according to one or more of the preceding aspects, and
- a container (30), provided with an inner cavity closable by the releasing stopper (1) for defining a predefined closed volume, wherein the container (30) comprises a closing counter-indicator (30*k*) positioned on one of its walls, and suitable for engaging with a closing indicator (10*k*) positioned on the releasing stopper (1) in at least a closing use configuration, wherein the engagement of the closing indicator (10*k*) on the stopper (1) determines a closing configuration of the container (30), optionally a complete closing of the container (30) and/or sealing and/or complete delimitation of the inner volume of the container (30).

According to another non-limiting aspect, the container (30) comprises a threading (34) in correspondence of which the stopper (1) removably engages itself and the closing counter-indicator (30*k*) is positioned in correspondence of and/or near the threading (34) of the container (30).

According to another non-limiting aspect, the threading (34) is realised in correspondence of a neck of the container (30), and/or in a portion of its substantial end. According to another non-limiting aspect, the container (30) is an outer threaded container, and/or is provided with an outer threading (34), realized on an outer face of the lateral surface of the container (30); optionally, the threading (34) extends radially towards the outside of the container itself.

According to another non-limiting aspect, the container (30) is an inner threaded container, and/or is provided with an inner threading (34), realized on an inner face of the lateral surface of the container (30); optionally, the threading (34) extends radially towards the inside of the container itself.

According to another non-limiting aspect, the stopper (1) comprises a counter-threading (10) suitable for engaging on the threading (34) of the container (30), and the closing indicator (10*k*) of the stopper (1) is positioned in correspondence of and/or near the counter-threading (10).

According to another non-limiting aspect, the stopper (1) is an inner threaded stopper and optionally the counter-threading (10) is positioned in correspondence of an inner face of an outer side wall of the stopper (1).

According to another non-limiting aspect, the stopper (1) comprises a cavity suitable for removably housing at least part of the container (30), in particular an ending portion of the container (30); the cavity (11) being optionally an annular cavity.

According to another non-limiting aspect, the inner face of the outer side wall of the stopper (1) faces the cavity (11).

According to another non-limiting aspect, the counter-threading (10) is positioned in correspondence of the cavity (11).

According to another non-limiting aspect, the guide portion (13*s*, 13*v*) comprises an annular wall (13*v*) innerly delimiting the cavity (11), in particular innerly delimiting the annular cavity (11).

According to another non-limiting aspect, the counter-threading (10) is positioned on the annular wall (13*v*).

According to another non-limiting aspect, in the closing configuration in which the closing indicator element is engaged with the closing counter-indicator (30*k*), there is at least a local elastic deformation of the container and/or of the stopper and/or of a portion of the wall of the stopper and/or of the container in correspondence of which the closing indicator element and/or the closing counter-indicator (30*k*) is present, and/or there is at least a local elastic deformation of the closing indicator and/or of the closing counter-indicator (30*k*).

According to another aspect, a method of opening of a releasing stopper (1) is described, optionally a releasing stopper (1) according to one or more of the preceding aspects, the method comprising:
- a step of introduction of a perforation or opening element (40, 41, 42) inside a container (30) through an opening of the container itself, wherein said opening is suitable for removably housing the releasing stopper (1), in such a way that this perforation or opening element (40, 41, 42) is removable from the container (30) and/or at least partially movable inside the container (30),
- a step of positioning of the releasing stopper (1) in substantial correspondence of the opening of the container (30), wherein
- as a result of the step of positioning of a closing element (15) suitable for allowing the opening of a reservoir (20) of the releasing stopper (1) is opened and/or fractured and/or broken by said perforation or opening element (40, 41, 42) allowing the release at least partial of a predefined quantity of a substance (S) contained inside the reservoir (S) inside the container (30) through the exercise of a force between the releasing stopper (1) and the container (30).

According to another aspect of the concepts herein, it is described a method of opening of a releasing stopper (1) suitable for and/or destined to be coupled removably with a container (30) and configured to contain and to selectively release a substance (S) in the container (30), wherein the stopper (1) comprises:
- a first body (1*a*) configured to be directly coupled with the container (30) and comprising a coupling element (10) suitable for allowing the removable fastening of the stopper (1) in correspondence of an opening of the container (30) defining a first mounting configuration of the stopper on the container wherein, preferably, the stopper closes the container (30);
- a closing element (15), constituting at least a portion of the reservoir wall (20) and facing the inside of the container (30) in the mounting configuration, the closing element (15) being configured to be selectively openable and/or breakable, defining at least a second open configuration of the stopper, through the action of a perforation or opening element (40, 41, 42) different from the stopper (1) and housed within the container, to make the reservoir (20) be in communication with the inside of the container (30); wherein the stopper (1) optionally comprising a closing indicator (10k), suitable for engaging on or in correspondence of a closing counter-indicator (30k) positioned on the container (30) determining a closing configuration of the container (30), the method comprising:

a step of introduction of the perforation or opening element (40, 41, 42) inside the container (30) through an opening of the container itself, wherein said opening is suitable for housing movably the releasing stopper (1), in such a way that this perforation or opening element (40, 41, 42) is removable from the container (30) and/or at least partially movable inside the container (30), a step of positioning of the releasing stopper (1) in substantial correspondence of the opening of the container (30), wherein as a result of the step of positioning the closing element (15) is opened and/or fractured and/or broken by said perforation or opening element (40, 41, 42) allowing the release at least partial of a predefined quantity of a substance (S) contained inside the reservoir (20) inside the container (30) through the exercise of a force between the releasing stopper (1) and the container (30).

According to another non-limiting aspect, the positioning step comprises the positioning of an ending portion of the perforation or opening element (40, 41, 42) in substantial contact with the closing element (15) of the releasing stopper (1), and the exercise of force between the releasing stopper (1) and the container (30) intended to cause the opening and/or fracturing and/or breaking of the closing element (15) comprises a compression, in particular an axial compression between the releasing stopper (1) and the container (30) in such a way that the ending portion of the perforation or opening element determines a failure of at least part of the closing element (15) and a subsequent reduction of an overall longitudinal extension of the assembly formed by the releasing stopper (1) and the container (30) and/or determines an introduction of the ending portion of the perforation or opening element (40, 41, 42) inside the reservoir (20) of the stopper (1).

According to another non-limiting aspect, the step of positioning comprises the direct coupling between the releasing stopper (1) and the container (30), with which their surfaces come into direct and reciprocal contact; optionally, the step of positioning comprising the direct coupling between the releasing stopper (1) and the container (30) with which reciprocal threadings (10, 34) come into direct contact and engage each other, and after the step of positioning the closing element (15) is opened and/or fractured and/or broken by the perforation or opening element (40, 41, 42) as a result and because of a step of screwing of the releasing stopper (1) on the container (30) wherein at least part of the stopper (1) rotates with respect to the container (30).

According to another non-limiting aspect, the perforation or opening element (40, 41, 42) comprises a rod (40) with a substantially axial development; said rod (40) being breakable in at least a predetermined position, in particular in a portion of weakening identified by a recess or notch.

According to another non-limiting aspect, the method comprises a step of fracturing of the rod (40), and the step of fracturing of the rod is carried out following the step of introduction of the perforation or opening element (40, 41, 42) inside the container (30).

According to another aspect, an element (40, 41, 42) for the collection and storage of biological and/or microbiological samples is described, comprising a rod (40) with a substantially axial development and a swab (42), optionally a flocked swab, realised in correspondence of an end of the rod or to which the rod (40) is solidly and/or rigidly attached; the element (40, 41, 42) for the collection and storage of biological and/or microbiological samples is characterized in that the rod (40) is at least partially hollow and is configured to allow the passage of a substance, in particular a fluid, between a first portion of the element for the storage of biological and/or microbiological samples (40, 41, 42) and a second portion in substantial correspondence or proximity to the swab (42) by passing the substance, in particular the fluid, between an inner cavity (41i) of the rod (40) and an outer surface of the rod (40) itself.

According to another non-limiting aspect, the element (40, 41, 42) for the collection and storage of biological and/or microbiological samples, comprises a first transfer duct (40k), optionally a first set of transfer ducts (40k) and at least a second transfer duct (40f), optionally a second set of transfer ducts (40f); the first transfer duct (40k) and the second transfer duct (40f), optionally the first set of transfer ducts (40k) and the second set of transfer ducts (40f), being in communication with the cavity (41i).

According to another non-limiting aspect, the first portion is an ending portion (41) of the rod (40) opposite the portion of the rod (40) in correspondence of which the swab (42) is positioned.

According to another non-limiting aspect, the cavity (41i) extends at least between:

a first height or portion of the rod (40) in correspondence of which the first transfer duct (40k) is located, optionally between a first height or portion of the rod (40) where the first set of transfer ducts (40k) is located, and a second height or portion of the rod (40) in correspondence of which the second transfer duct (40f) is present, optionally a second height or portion of the rod (40) in correspondence of which the second set of transfer ducts (40f) is present.

According to another non-limiting aspect, the element for the collection and storage of biological and/or microbiological samples (40, 41, 42) is configured and intended to cause the at least partial leakage of the substance (S), in particular of the fluid, from a reservoir of a releasing stopper, optionally from a reservoir of a releasing stopper according to one or more of the aspects here described.

According to another non-limiting aspect, said releasing stopper is a stopper (1) comprising:

a first body (1a) configured to be directly coupled with a container (30) for biological and/or microbiological samples, the first body (1a) comprising a coupling element (10) suitable for allowing the removable fixing of the stopper (1) in correspondence of an opening of the container (30) defining a first mounting configuration of the stopper on the container wherein, preferably, the stopper closes the container (30);

a closing element, optionally a membrane (15) or collapsible septum, constituting at least a portion of the reservoir wall (20) and facing the inside of the container (30) in the mounting configuration, the closing element, optionally the membrane (15) or collapsible septum, being configured to be selectively openable and/or breakable, defining at least a second open configuration of the stopper, through the action of the element for the collection and storage of biological and/or microbiological samples (40, 41, 42), optionally when housed inside the container, to put the reservoir (20) in communication with the inside of the container.

According to another non-limiting aspect, the first transfer duct (40*k*), optionally the first set of transfer ducts (40*k*), is positioned at a height such that, when the rod (40) is introduced into the reservoir of the releasing stopper, it is located inside said reservoir.

According to another non-limiting aspect, the first transfer duct (40*k*) coincides with the cavity (41*i*) and/or the first transfer duct (40*k*) is axial to the cavity (41) and/or the cavity (41*i*) extends up to an ending portion of the rod (40) opening on a head portion of the rod.

According to another non-limiting aspect, the first set of transfer ducts (40*k*) is radially arranged on the rod (40) and/or the second set of transfer ducts is radially arranged on the rod (40).

According to another non-limiting aspect, the second transfer duct (40*f*), or the second set of transfer ducts (40*f*), is arranged at a height at which the swab (42) is present, and/or is overhung and/or surrounded by the swab (42).

According to another non-limiting aspect, the second transfer duct (40*f*), or the second set of transfer ducts (40*f*), is placed in correspondence of a portion of the rod (40) different from the portion of the rod (40) in correspondence of which the swab (42) is present.

According to another aspect, it is described a kit comprising a releasing stopper (1) according to one or more of the aspects here described and an element for the collection and storage of biological and/or microbiological samples (40, 41, 42) according to one or more of the aspects here described.

According to another non-limiting aspect, the kit also comprises a container (30) configured to be closed through the releasing stopper (1).

According to another non-limiting aspect, the container (30) is a container according to one or more of the aspects here described.

BRIEF DESCRIPTION OF DRAWINGS

The object of the present disclosure will be now described in preferred and non-limiting embodiments described with the support of the attached figures, wherein:

FIG. 1 shows a lateral view of a stopper in accordance with the present disclosure, coupled with a container to contain and/or store a biological sample;

FIG. 2 shows a lateral view of a first body of the stopper object of the present disclosure;

FIG. 3 shows a lateral view of a second body of the stopper object of the present disclosure;

FIG. 4 shows a sectioned view of the second body of the stopper, where the section is taken along the A-A lines of FIG. 3;

FIG. 4*a* shows a first realization variant of a radially outer portion of the second body;

FIG. 4*b* shows a second realization variant of a radially outer portion of part of the second body;

FIG. 5 shows a sectioned view of the first body of the stopper, where the section is taken along the A-A lines of FIG. 2;

FIG. 5*a* shows a detail of part of FIG. 5, observed along a section orthogonal with respect to the section of FIG. 5;

FIG. 6 shows a detail of section of FIG. 5;

FIG. 9 shows a detail section of the first body and of the second body of the stopper, when in the configuration of maximum axial extension;

FIG. 10 shows a section of the container to contain and/or store a biological sample, provided with an element for the collection and storage of biological material and provided with a rod and a swab;

FIG. 11 shows an intermediate operating configuration in which the rod of the element for the collection and storage of biological material is in proximity to a membrane that is part of the first body of the stopper;

FIG. 12 shows an intermediate operating configuration, in which the rod has broken the membrane, which is partially inclined with respect to the longitudinal axis of the stopper, and in which this configuration is temporally subsequent to the one shown in FIG. 11;

FIG. 13 shows a configuration subsequent to the one shown in FIG. 12, in which the membrane, now broken, is trapped between the rod of the element for the collection and storage of biological material and a shoulder realized on the first body;

FIG. 14 shows a sectional view of the stopper-container assembly, in which the rod positioned within the container and partially introduced within the first body of the stopper is observed;

FIG. 15 shows a sectional view of the stopper-container assembly, in which the substance deposited on the bottom of the container is observed, following the breaking of at least one membrane;

FIG. 16 shows a detailed sectional view corresponding to FIG. 15, in which the first body 1*a* and the second body 1*b* are reciprocally in a configuration of minimum axial extension;

DETAILED DESCRIPTION

Figure 8:
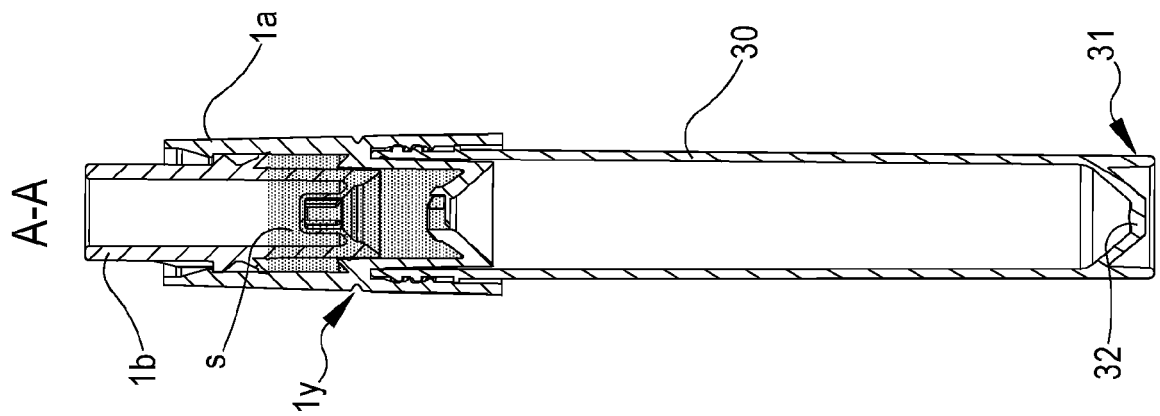
FIG. 8 shows a sectional view along the A-A lines of FIG. 1, in which it is possible to observe the stopper object of the present disclosure in a configuration of maximum axial extension and in a closed configuration, in which it stores a substance S.
Figure 7:
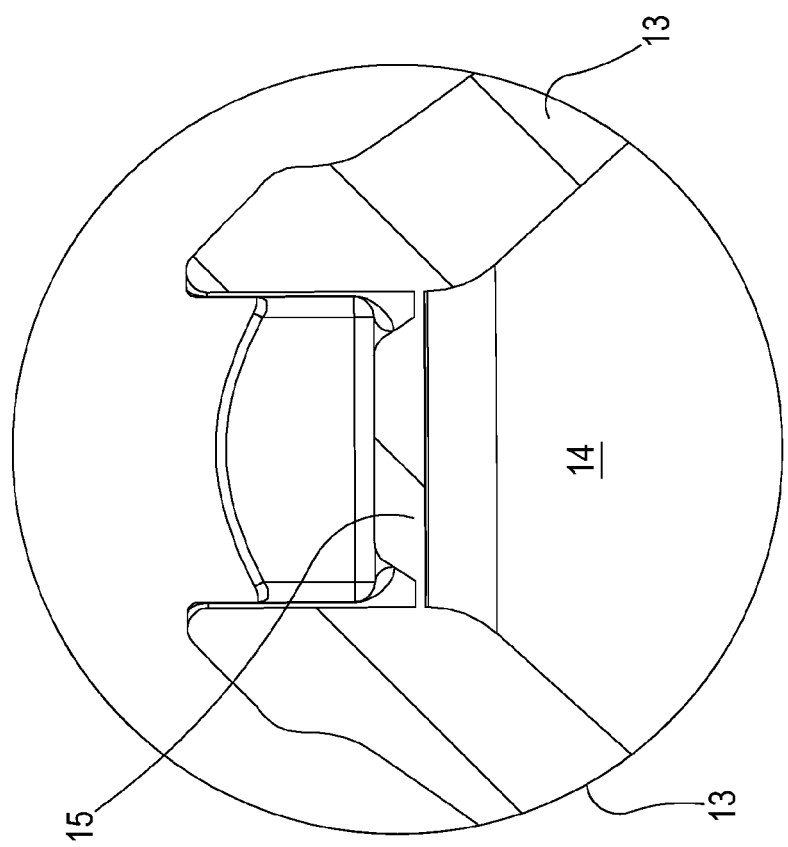
FIG. 7 shows a further detail of section of FIG. 5.

The present disclosure shows a releasing stopper 1 suitable for, in particular intended to be coupled with a container 30, for example and non-limiting to a test tube, to contain and/or store a biological sample, possibly to be submitted in a subsequent moment to one or more analysis. In particular, the coupling between the stopper object of the present disclosure and the container 30 occurs in correspondence of an opening of the container itself, which in an embodiment here described—and represented in the attached figures— also represents the only opening of the container itself. This opening is in a head portion of the container 30, and the releasing stopper 1 is configured and/or is intended to be removably coupled against the head portion.

The releasing stopper 1 object of the present disclosure is called "releasing stopper" because it is configured to contain a substance S inside one of its reservoirs, and release in a predetermined way, the substance S from its reservoir to the container 30. The substance S contained in the reservoir is a substance which can be either fluid, in particular liquid, or in solid form, e.g. in granular and/or powdered form.

The substance S previously described can be or comprise, in addition to solid and liquid, also a gelatinous substance, and/or can comprise Newtonian and/or non-Newtonian fluids, and/or can be or comprise gases or vapours. Therefore, the stopper object of the present disclosure is capable to contain any form of matter without limitation. In particular, the stopper object of the present disclosure can also be suitable for and/or intended to contain a substance S emitting ionizing radiation.

FIG. 1 shows a stopper with a first and a second body respectively indicated with references 1a and 1b, movable the one with respect to the other according to a main sliding direction identified in particular by the axis X of the stopper 1 itself. The axis X represents the longitudinal axis of the stopper, and for convenience of description will also be considered the longitudinal axis of the container 30. In detail, the first body 1a is configured to directly engage on the container 30, in a centred way with respect to the axis X. The coupling that is realized between the first body 1a and the container 30 is such that the first body 1a is configured to be rigidly united and/or fastened on the head portion of the container 30, that is to say to strike against the head portion of the container 30.

In the present description it will be made sometimes reference to the heights assumed by parts and components; where the heights are outlined as minimum and maximum, these heights will be intended in relation to the portions as represented in the attached figures, in particular having the container 30 vertically arranged with the stopper 1 positioned on the head. The heights can also be defined as inner and outer in relation to different portions of the stopper or container, in particular the ending portions of themselves.

In the embodiment here described the second body 1b slides with respect to the first one by a linear translation along said axis X, but this configuration is not to be understood in a limiting way because the reciprocal movement, in particular the reciprocal sliding between the first body 1a and the second body 1b can take place by a composed movement in which the resulting translation along the axis X is given by a screwing or rotation of the second body 1b on a counter-threading realized on the first body 1a.

The stopper 1 presents a first operating configuration in which it is suitable for containing a substance inside a reservoir 20 of limited volume, and in which the reservoir 20 is closed with respect to the outer environment, and a second operating configuration in which it is suitable for releasing the substance contained inside the reservoir 20 in the outer environment. The reservoir 20 is defined by a coupling between the first body 1a and the second body 1b, in particular being generally laterally confined by the inner face of the side wall of the first body 1a, below by a wall of the first body 1a and a collapsible septum, and upperly by a portion of the body 1b that enters into contact—in particular seamlessly—with the inner face of the lateral wall of the first body 1a.

As it will be better described in the following portion of description, the release of the substance S from the reservoir 20 to the outer environment takes place, in a preferred although non-limiting operating configuration, with a release inside the container 30. In the preferred embodiment the relative mobility existing between the first body 1a and the second body 1b of the stopper is such that a plurality of relative positions can be assumed between a configuration of maximum axial extension of the stopper 1 and a configuration of minimum axial extension of the stopper 1. Preferably, the position of maximum axial extension is part of the first operating configuration, while the second operating configuration comprises the configuration of minimum axial extension. In any case, both the first operating configuration and the second operating configuration comprise intermediate axial extension configurations between the maximum axial extension configuration and the minimum axial extension configuration. The maximum axial extension configuration is also the rest configuration for the stopper 1. This determines that the switching between the first operating configuration and the second operating configuration takes place in an intermediate axial extension configuration between the minimum and the maximum one. In other words, the second open configuration takes place in correspondence of a longitudinal extension comprised, preferably substantially intermediate, between the longitudinal extension corresponding to the maximum extension configuration and the longitudinal extension corresponding to the minimum longitudinal extension configuration. This aspect allows particular safety of use, because it prevents, for example, that minimum actions on the body of the stopper that cause an axial compression can inadvertently determine an immediate switch between the first and second operating configurations.

The transition from the first operating configuration to the second operating configuration is given by the breaking of at least a closing element that in the embodiment here described and in particular represented in the attached figures is a membrane 15 or collapsible septum selectively openable and/or breakable and/or perforable, which in the first operating configuration is therefore intact and extends seamlessly to define a wall or portion of wall that contributes, with other walls, to delimit the volume of the reservoir 20; in the second operating configuration the membrane 15 or collapsible septum, for at least a portion of it, no longer shows continuity with the walls with which it is arrived, and therefore allows the release of the substance inside the container 30.

The membrane 15, or collapsible septum, is installed on the first body 1a and is part of the first body 1a itself; at least when in closed configuration, this membrane 15, or collapsible septum, is integral to the first body 1a.

The membrane 15, or collapsible septum, is impermeable to liquids and/or gases, and therefore constitutes a barrier.

Therefore, the stopper 1, which is the object of the present disclosure, is a stopper in which the breaking of the membrane 15 or collapsible septum is given by an outer element, removably positionable within the container 30, which constitutes for the purposes of the present disclosure an element of perforation or opening of stopper 1, and more in particular of perforation or opening of the membrane 15 or collapsible septum, which is identified as a whole by the numerical references 40, 41, 42; this perforation or opening element is in particular an element for the collection and storage of biological and/or microbiological samples, and what actually determines the breaking of the membrane 15 or collapsible septum is an ending portion of the aforementioned element. Therefore it is not caused, nor can it be caused, by a component of the stopper itself, but, on the contrary, by an element distinct from the container and/or movably, in particular removably, housed inside the container.

The membrane 15 or collapsible septum here described is not replaceable in its closing configuration, and once opened or otherwise broken can no longer be reconfigured in a configuration that allows the new closing of the reservoir 20; consequently, this makes the stopper 1 object of the present disclosure a disposable stopper. After the membrane 15 or collapsible septum has been opened or fractured or otherwise broken in the manner that will be described, the closed configuration of reservoir 20 can no longer be restored.

As represented in FIG. 11 and FIG. 5, it is possible to observe that the first body 1*a* has an upper cavity 1*c* and a lower cavity 14 separated from each other by the presence of the membrane 15 or collapsible septum positioned in correspondence of a short channel that seamlessly connects the reservoir 20 with the lower cavity 14; within the upper cavity, due to the coupling with the second body 1*b*, it is realized the reservoir 20 suitable for containing the aforementioned substance. The upper cavity 1*c* is divided in two portions identified with the references 1*r* and 20'; the first portion (upper) of the upper cavity faces directly on the upper opening of the first body 1*a*; the second portion (lower) of the upper cavity 1*c* is situated in a zone substantially central of the first body and is in communication with the first portion but, according to the present disclosure, it is ideally divided from it in correspondence of an undercut that will be better defined in the following portion of description.

The upper portion presents a lateral surface substantially cylindrical having a first diameter; the lower portion presents a lateral surface substantially cylindrical or slightly flared, having a diameter in any case lower than the diameter assumed by the upper portion.

The first body 1*a* outerly comprises a lateral wall provided with a gripping portion 1*z* preferably characterized by knurling, with ribs arranged substantially along the direction identified by the axis X (as represented in the attached figures) or crossed (solution not represented) or more generally by elements suitable for facilitating the friction of the user's fingers at least at the coupling of the stopper here described on the container 30. The gripping portion 1*z* is also useful to facilitate the gripping of a manipulator or a spindle, for example an automatic handling machine. In the configuration shown in the attached figures, this gripping portion 1*z* is at the base section of the lateral wall. Otherwise, the upper section of the outer face of the lateral wall of the first body 1*a* is preferably but non-limiting smooth.

Between the lower section and the upper portion of the above mentioned outer band, the Applicant has realized an annular recess 1*y*, preferably defined on a connection curve whose cavity is without angular points and/or extending along the entire perimeter of the lateral surface of the lateral wall of the first body 1*a*; this annular recess 1*y* is advantageously conceived in order to standardize the cooling of the first body 1*a* at the time of realization. The Applicant has observed in fact that the portion of lateral wall in substantial correspondence of the annular recess 1*y* is the one of greater thickness, and it is therefore the one that in the cooling following the fusion or the moulding of the plastic material with which the first body is realized, would be the one that is cooled later, resulting still at a temperature sensitively greater with respect for example to the upper and lower ending portions of the same body. The Applicant has found that this difference in cooling time can lead—especially in case of areas with high thickness and/or density of material—to the formation of cracks even not visible that can weaken the structure of the product and/or lead to the leakage of part of the substance contained in the reservoir 20. Such recess 1*y* has therefore the task to reduce the quantity and/or density of material in the longitudinally central zone of the first body 1*a*, contributing to guarantee the final robustness of the body itself. The annular recess 1*y* is preferably present, but its presence does not have to be understood as limitingly mandatory.

The above-mentioned plastic material, with which the first body is realized, is a plastic material resistant to acids and/or corrosive substances, in particular those that can be contained inside the reservoir 20, and is preferably even if non-limiting thereto a biocompatible material and i.e. of nature such that not to release substances when in contact with biological samples.

By observing the first body 1*a* in section, it is possible to notice how the lateral wall, in substantial axial correspondence of the gripping portion 1*z*, faces an annular cavity 11 within which there is a counter-threading 10 able to engage in use on a threading 34 present on the outer face of the upper portion 33 of the lateral wall of the container 30. This portion identifies a head portion of the container 30. The annular cavity 11 is configured to house at least part of the container 30, in particular a portion of the end of the container. The gripping portion 1*z* is realized in correspondence of a portion of the outer lateral wall of the first body 1 that presents, in turn, an outer face (the one where the gripping portion is present) and an inner face, the latter facing the annular cavity 11. In the embodiment illustrated in the attached figures, the counter-threading 10 is realized on this inner face of the outer side wall of the first body 1*a*. The stopper 1 object of the present disclosure therefore has an inner threading. The threadings present on the stopper and on the container 30 realize a non-exhaustive example of coupling elements between the stopper and the container, wherein the closing of the container is determined by a first of all rotating movement of at least part of the stopper 1 in relation to the container 30 (in particular a rotation around the longitudinal axis X) which translates, precisely because of the threading, into a linear translation along the longitudinal axis X of the stopper 1 in relation to the container itself. The first body 1*a* also has a guide portion 13*s*, 13*v*, suitable to guide and hold at least temporarily a rod 40 of an element for collecting and/or storing biological samples. The counter threading 10 realizes a removable coupling element to allow the temporary fixing of the stopper 1 on the container 30.

The rod 40 here described, and represented in the attached figures, is a body of substantially elongated shape that in a particular embodiment is provided with a swab 42, for example and non-limiting to flocked material. In a particular embodiment this swab 42 can be configured to be separated from the rod 40 in correspondence of one or more weakening portions positioned on the body of the rod 40 itself, which can be extended also inside the swab 42.

The annular cavity 11 has a circular crown section whose maximum (or outer) radius is given by the inner face of the lateral wall of the body itself, and whose minimum (or inner) radius is given by the guide portion 13*v*, 13*s*.

This guide portion 13*s*, 13*v* in particular comprises a first annular wall 13*v* (which, when observed in plain view, identifies an outer perimeter substantially circular) that substantially extends along the direction identified by the axis X and a second flared wall 13*s*, and preferably with circular section, suitable for identifying a recess 14 in the shape of a funnel, convex towards the inside of the first body 1*a* and concave towards the outside, which realizes a tapered element or portion, in particular accessible from the inside of the container 30, suitable for directing an ending portion of the rod 40 towards the opening obstructed by the membrane 15 or collapsible septum. The annular wall 13*v* contributes to delimit the annular cavity 11, in particular by delimiting its inner profile.

Figure 17:
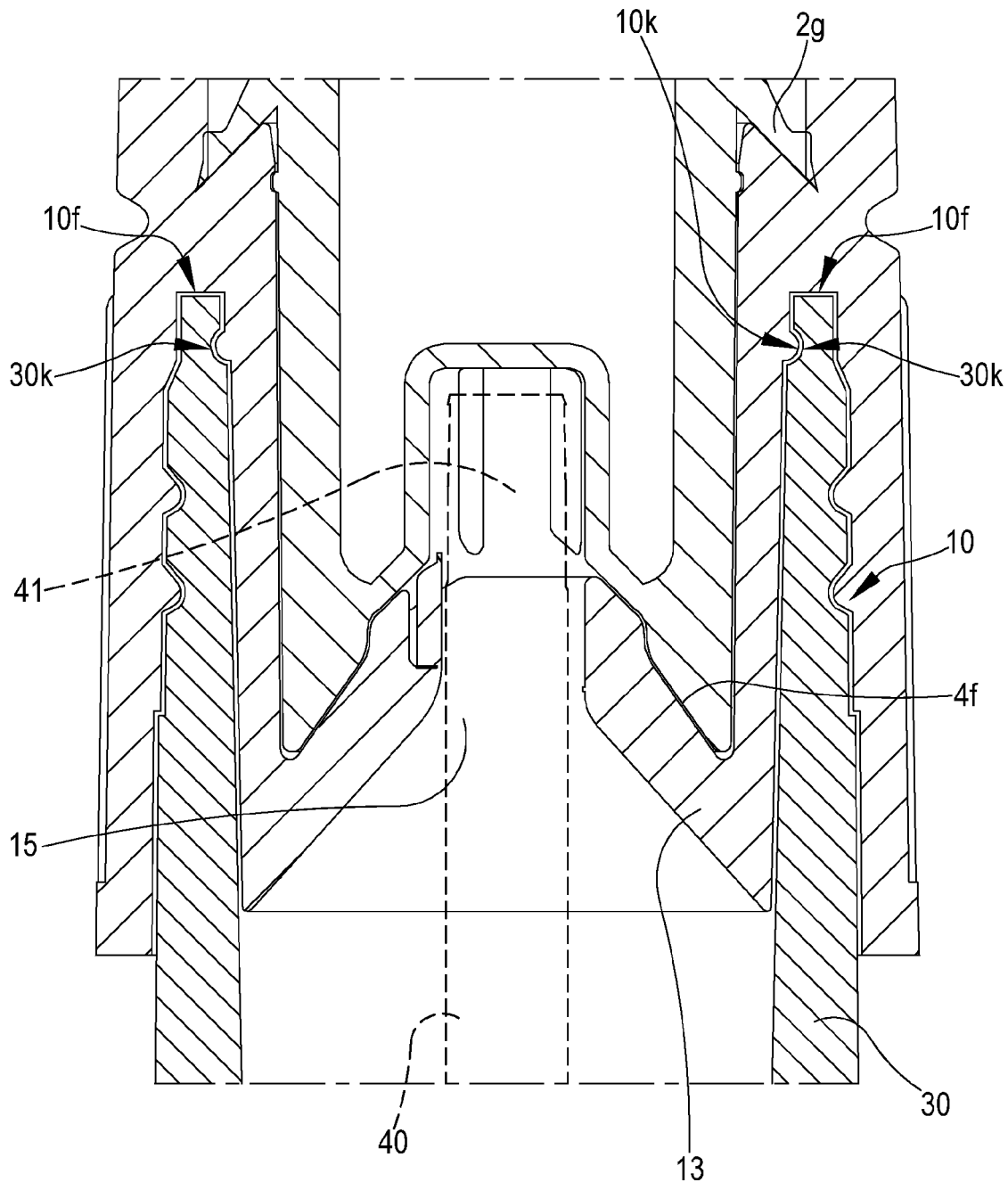
FIG. 17 shows a detail of a sectional view of the releasing stopper when coupled with a container.

As shown in detail in FIG. 17, in correspondence of a predetermined portion of the first annular wall 13*v*, preferably in correspondence of an upper portion of the annular wall 13v, there is a ring 10k that extends substantially with a semi-circular profile from the outer face of this annular wall 13v. The ring 10k, positioned near the counter-threading 10 of stopper 1, is integral and/or part of the annular wall 13v itself, and is in particular realized with the same material deriving in fact from the manufacturing process of the first body 1a. Therefore, this ring 10k is seamlessly joined to the annular wall 13v. This ring 10k is designed primarily in order to optimize the closing of the stopper 1 on the container 30, and is in particular designed to fit into a corresponding recess on the neck of the container 30. This recess, when the ring 10k has a semi-circular profile, has a concavity in turn of semi-circular shape.

In use, when it is carried out a step of screwing in which the stopper 1 is screwed on the container 30, the completion of the screwing is given by the engagement of the ring 10k on the recess present on the neck of the container 30 itself. When the ring 10k, and consequently the annular wall 13v, are realized with sufficiently rigid plastic material, at the moment of the engagement of the ring 10k on the recess present on the neck of the container 30, a sound can be heard, in particular a "click" that helps the operator to understand that the completion of the screwing has been achieved.

In a preferred and non-limiting embodiment of the stopper object of the present disclosure, the completion of the screwing of the stopper on the container 30 is given by the introduction of the ring 10k in correspondence of the corresponding recess on the neck of the container 30 and by the contact of a bottom wall of the annular cavity 11 against the upper edge of the container 30. Preferably, as represented in the attached figures, the back wall of the annular cavity 11 is substantially arranged in the orthogonal direction with respect to the axis X.

The Applicant points out that the presence of a ring 10k configured to determine a completion of a closing of a stopper with respect to a container can also ignore the presence of the second body 1b movable with respect to the first body 1a. For this reason, according to the present disclosure, a releasing stopper 1 can be designed to be suitable for and/or designed to be removably coupled with a container 30 and configured to contain and selectively release a substance S in the container 30, in which the stopper 1 comprises:

a first body 1a configured to be directly coupled with the container 30 and comprising a coupling element 10 suitable for allowing the removable fixing of the stopper 1 in correspondence of an opening of the container 30 defining a first mounting configuration of the stopper on the container wherein, preferably, the stopper closes the container;

a closing element 15, constituting at least a portion of the reservoir wall 20 and facing inside the container 30 in the mounting configuration, the closing element 15 being configured to be selectively openable and/or breakable, defining at least a second open configuration of the stopper, through the action of a perforation or opening element 40, 41, 42 distinct from the stopper 1 and housed inside the container, to put the reservoir 20 in communication with the inside of the container; wherein:

the stopper comprises a closing indicator 10k, suitable for engaging on or in correspondence of a closing counter-indicator 30k placed on the container 30 determining a closed configuration of the container 30.

In particular the closing indicator 10k is represented by the aforementioned ring, while the closing counter-indicator element is represented by the aforementioned recess positioned on the neck of the container 30. The Applicant points out that an opposite configuration can also be realized, wherein on the neck of the container 30 there is the ring 10k while on the stopper 1 there is the corresponding recess. Both these configurations fulfil the abovementioned technical effect.

It can also be defined a kit, which in addition to the releasing stopper 1 in the previously mentioned configuration, comprises a container 30, provided with an inner cavity closable by the releasing stopper 1 to define a predefined closed volume, wherein the container 30 comprises a closing counter-indicator 30k placed on one of its walls, and suitable for engaging with a closing indicator 10k positioned on the stopper 1 in at least one closing use configuration, wherein the engagement of the closing indicator 10k on the stopper 1 determines a closed configuration of the container 30, optionally a complete closing of the container 30 and/or sealing and/or complete delimitation of the inner volume of the container 30.

It is to be noted that the above mentioned combination of closing indicator element closing counter-indicator 30k in the various alternatives can realize an element suitable for realizing the sealing and complete delimitation of the inner volume of the container 30 in particular when the wall of the stopper and of the container on which they are reciprocally arranged (or alternatively or in combination their specific realization and/or constituting material) are such to allow a relative elastic deformation such that in the closing configuration wherein the closing indicator element is engaged with the closing counter-indicator 30k, there is at least a local elastic deformation of the container and/or of the stopper and/or of a portion of the wall of the stopper and/or of the container in correspondence of which the closing indicator element and/or the closing counter-indicator 30k is present, and/or there is at least a local elastic deformation of the closing indicator and/or of the closing counter-indicator 30k. In the specific case of the embodiment of the releasing stopper 1 described in the present disclosure, this elastic deformation can be made possible by the fact that the body of the stopper 1 and of the container 30 are realized in plastic, and can be helped by the fact that the closing counter-indicator 30k represented by the annular recess is positioned in correspondence of the neck of the container 30, therefore in a normally open area susceptible to have a certain degree of elasticity. This elastic deformation is the one that allows to obtain a contact between the stopper 1 and the container 30 such that a force is developed substantially in a transversal direction, preferably orthogonal, with respect to the longitudinal axis X, such as to allow a safe sealing of the inner volume of the container 30.

The presence of the combination closing indicator 10k-closing counter-indicator 30k should not be intended as limiting, since the closing indicator 10k could also rest on the inner face of the lateral surface of the container 30 also in an alternative embodiment, wherein this inner face is without the closing counter-indicator 30k, in any case fulfilling the technical effect of assisting the sealing and/or the complete closing of the cavity of the container 30 itself.

As it can be seen from the attached figures, the funnel-shaped recess 14 is placed in a longitudinally outer position with respect to the membrane 15 or collapsible septum, the latter resulting in a more backward position, or equivalently at a greater height, with respect to the height at which the recess 14 is located. This opening, has a diameter slightly larger than the diameter assumed by the rod 40. The upper portion of the rod 40 is precisely the outer element previously mentioned that can cause the breaking of the membrane 15 or collapsible septum. In detail, the membrane 15 or collapsible septum extends orthogonally with respect to the axis X and is preferably, although non-limiting thereto, realized as an integral portion of the second wall 13s, and is therefore substantially rigid and strong enough to withstand the pressure that can be induced by the action of the operator on the second body 1b, at least accidentally. The second wall 13s is provided with an inner face that identifies a bottom wall of the reservoir 20, which is delimited laterally by a wall of circular or cylindrical section.

The second wall 13s is flared in such a way that moving along the axis X towards the base of the stopper 1, the diameter of the circumference identified by it along a section taken on a plane orthogonal to the aforementioned axis X, appears gradually increasing. In other words, the wall 13s is convex upwards, i.e. towards the head portion of the first body 1a.

The lateral wall of the first body 1a extends seamlessly until the head of the body itself, and identifies an upper recess that corresponds to the upper cavity and that is delimited at the bottom by the second wall 13s, precisely by its upper face and by the cavity in which the membrane 15 is present. The upper recess is suitable for housing least part of the second body 1b and presents a shape such as to allow the sliding respect to the first body 1a. In particular, as observable for example in FIG. 15 or FIG. 16, the upper cavity 1c has a size such as to house all the second body 1b when in the configuration of minimum axial extension of the stopper 1.

In correspondence of the ending, the upper cavity 1c presents a tapered portion configured to allow the introduction by contrast at least part of the second body 1b and also configured to cause the retention of at least part of the second body 1b within the upper recess. Such tapered portion 1i allows therefore to delimit the stroke of the second body in the sense of the configuration of maximum axial extension, causing indirectly the definition of the maximum volume assumable by the reservoir 20 when the stopper 1 is in the aforesaid configuration of maximum axial extension. By observing the upper cavity 1c in a section orthogonal to the axis X it is possible to verify that moving from the upper ending towards the membrane 15 or collapsible septum, after a first subsection with constant diameter, the light of said upper recess gradually reduces, with circumferences of diameter gradually reducing until reaching a predetermined depth height within the same upper recess 1r. Such predetermined depth height is schematically indicated in FIG. 5 and in FIG. 16 with the reference Q. The inner face 23 of the lateral wall of the first body therefore identifies a tapered section surface that ends in correspondence of a shoulder 24 with an annular portion of wall oriented along a plane substantially orthogonal to the direction identified by the axis X, that determines a stopping point for a portion of the second body 1b. The latter, when introduced by introduction by contrast, in particular with elastic deformation of one of its elements, inside the upper recess 1r, after the aforementioned shoulder 24 can no longer be extracted from the recess 1r itself. The reduction of the diameter induced by the shoulder 24 is such as not to cause plastic deformation of any part of the second body 1b when introduced in the first body 1a.

As already mentioned, between the first and the second section of the upper cavity there is a "V"-shaped undercut 17, annular shaped, which is configured to house a portion of the second body 1b, in particular when the stopper 1 is in the configuration of minimum axial extension. This V-shaped undercut 17 acts as a stop for the aforesaid portion of the second body 1b, so that with the progressive reduction of the axial extension of the stopper 1b induced by the introduction of the second body 1b within the body 1a such portion of the second body 1b arrives in contrast with the vertex of the V formed by the undercut 17 causing the stop of the sliding of the second body 1b along the aforesaid longitudinal axis X.

The Applicant observes that in the configuration of maximum axial extension the shoulder 1s present on the outer lateral surface of the second body 1b is positioned against the shoulder 24 present on the inner lateral surface of the first body 1a and that, in such a configuration, part of the lower portion 28 of the second body 1b is partially introduced within the lower section of the upper cavity of the first body 1a.

The Applicant has observed that during the step of mounting, unintentional pressures can occur in the reservoir 20 induced by the coupling of the second body 1b on the inner surface of the lower section previously mentioned. In order to reduce the negative effect of such pressure, the Applicant has provided the upper section, in particular the head section of the first body 1a, with a pressure relief cut identified in FIG. 11 with the reference number 29; this pressure relief cut is preferably, although non-limiting thereto oriented in a direction substantially parallel to the direction identified by the axis X, and configured in such a way as to allow the discharge of the pressure inside the reservoir 20 in a non-operational condition, i.e. during the mounting, without affecting the tightness of the reservoir 20 itself when at least the configuration of maximum axial extension has been reached.

In a particular non-limiting embodiment, the stopper object of the present disclosure presents selective block elements specifically configured to cause a block of the movement of the first body in relation to the second body when in a configuration different from the closed configuration and/or different from the configuration of maximum axial extension and/or following the opening of the reservoir 20. These elements of selective block can comprise for example an annular notch 20k positioned in substantial correspondence of the V-shaped undercuts 17, and in particular on the inner face of the lateral wall of the lower section 20'; this notch 20k is advantageously configured to allow to house a contrasting ring 28p that when present extends radially from the lateral surface of the lower portion 28 of the second body 1b. Such striking ring realizes also part of said selective block elements. In a preferred, and non-limiting, embodiment, the concavity assumed by the annular notch 20k is of equal shape and contrary to the convexity assumed by the contrasting ring 28p. The contrasting ring 28p and the annular notch 20k cooperate with each other in order to allow that, when the stopper is in the configuration of minimum axial extension, the contrast introduction of the contrasting ring 28p inside the annular notch 20k determines a locking of the stopper in the above configuration of minimum axial extension. Thanks to this aspect, it is possible to prevent the unintentional return of the stopper in axial configurations of greater axial extension, for example through a pop-out induced by pressure increases inside the container and/or pressure reductions in the outer environment that could occur, for example, if the container with the stopper screwed on is brought to altitude or in an airplane. Also, thanks to this aspect, it is possible to make the "used" stopper always provided with the same outer, univocal geometry, compatible with automatic handling devices of containers for biological material, which for example through mechanical or optical sensors are able to detect the difference in size between a stopper where the substance S is still in the reservoir 20 and a stopper "used", where due to the axial compression between the first and second body there is a reduction in size of the stopper itself. In particular, this aspect allows the possibility of easy handling of the stopper 1 through automatic uncorking devices.

In a particular embodiment, represented in the figures attached to the present description, the lateral wall of the reservoir 20 is not perfectly cylindrical, but is flared; the diameter of its section—along a plane orthogonal to the axis X—is gradually reduced as we proceed from the head portion towards the second wall 13s.

The breaking of the membrane 15 or collapsible septum through the upper portion of the rod 40 occurs in the modes described in detail below and shown in FIGS. 11, 12 and 13.

The breaking of the membrane 15 or collapsible septum is achieved by using an upper portion of the rod 40 previously placed inside the container 30, as schematically shown in FIG. 10. In this first step, the membrane 15 or collapsible septum is intact, as shown in FIG. 11.

The breaking of the membrane 15 or collapsible septum is given by a ratio, in particular a dimensional difference between the longitudinal development of the container 30 and the longitudinal development of the rod 40, more precisely by a difference in the longitudinal development along the axis X of the axial extension of the container 30 along the axis X with respect to the axial extension of the rod 40 along the same axis. The length of the rod 40 must be sufficient so that, when it is introduced inside the container 30, it can interfere with the membrane 15 or collapsible septum so that it can open or fracture it.

In a non-limiting embodiment, the progressive screwing of the threading 10 of the stopper 1 onto the threading 34 on the outer face of the lateral wall of the container 30 determines a progressive approach of the stopper 1 towards the rod 40 itself; the upper portion of the rod is guided by the wall 13s towards the opening where there is the membrane 15 or collapsible septum. Here it is pointed out that the guide exerted by the lateral wall 13s is properly given by its conformation and does not require particular attention by the user. Thanks to this aspect, rods 40 also not axially aligned along the axis X and/or inclined with respect to the axis X can be properly precisely guided towards the opening where there is the membrane 15 or collapsible septum through the simple and progressive screwing of the stopper on the container. With the progressive screwing, a condition is reached in which the upper end of the rod 40 comes in mechanical contrast with the membrane 15, and a subsequent and further screwing of the stopper determines the breaking of the membrane 15 or collapsible septum (this situation is schematically represented in FIG. 12).

At this point, this breaking determines the opening of the reservoir 20 previously described with the consequent direct communication of the reservoir 20 with the container 30.

In the above described embodiment, therefore, the mere support of the stopper 1 on the container 30 is not sufficient to cause the breaking of the membrane 15 or collapsible septum so as to allow the opening of the reservoir 20.

In an embodiment alternative to the previous one, when the stopper 1 is neared to the container 30, before an engagement of the threading 10 on the threading 34 of the stopper 1 can be realized, the stopper 1 remains "resting" on the rod 40, in particular on its opposite end portion with respect to the portion where there is the swab. In particular, this support can be given by the fact that the rod 40 is long enough to extend out of the shape identified by the container 30. The support is made with the end portion of rod 40 resting on membrane 15 or collapsible septum. The weight of the stopper 1 is not sufficient to cause a breaking of membrane 15 or collapsible septum. An additional pressure on the stopper, particularly on the first body 1 of the stopper itself, is required to break the membrane 15 or collapsible septum by opening the reservoir 20. At this point an intrusion of part of the rod 40 within the first body 1a is realized, which determines the possibility to join the threading 10 on the threading 34 of the stopper 1. The progressive screwing of the first body 1a of the stopper 1 on the container 30 determines a progressive and always greater introduction of the rod 40 within the first body 1a.

The Applicant points out that the diameter of the membrane 15 or collapsible septum, or equivalently the diameter of the opening delineated by the second wall 13s, is greater, in particular significantly greater, than the diameter of the portion of the rod 40 that is introduced into it; thanks to this aspect it is possible to have a leakage of liquid or equivalently the passage of the substance from the reservoir 20 to the container 30. Although in the present disclosure it has been discussed so far about the diameter in relation to the membrane 15 and to the body of the rod 40, it must be understood that the latter could have a different shape from the circular one, for example being polygonal, in which case the size of the opening should be anyway greater than the size of the section that the portion of the rod 40 that is introduced has along a plane orthogonal to the axis X. Between the opening and the body of the rod 40 there is not a introduction by contrast, but a substantially free introduction, in which, incidentally, the rod 40 is free to rotate or has clearance within the opening itself. The Applicant has observed that in use, particularly when dealing with samples of biological material, there is a need to prevent unwanted material from being dispersed inside the container 30. Among this unwanted material, is comprised the membrane 15 or collapsible septum, which therefore, when broken, is advantageously kept inside the stopper 1 object of the present disclosure. Among the technical solutions suitable for achieving this effect, the Applicant has realized the membrane 15 or collapsible septum in the shape of a thin plastic wall, arranged orthogonally to the axis X, and designed to break without releasing fragments. In addition to this aspect, the Applicant has designed the membrane 15 or collapsible septum in a non-uniform and/or non-symmetrical shape, but provided with a weakening portion, preferably in a position corresponding to the joint with the lateral wall of the opening. The weakening is preferably realized by reducing the local thickness of membrane 15 or collapsible septum itself.

Optionally, but non-limiting thereto, the stopper 1 object of the present disclosure comprises a retaining element of membrane 15 or collapsible septum, configured to prevent the membrane from releasing and/or falling into the container 30. In the embodiment represented in the attached figures, this retaining element comprises a shoulder realized near the channel that connects the reservoir 20 with the outside. In detail, the channel to which the membrane 15 or collapsible septum gives access has been provided with a shoulder 15s suitable for containing the membrane 15 or collapsible septum bent so as to be substantially positioned in a plane parallel to the axis X. This shoulder is preferably diametrically opposed to the weakening portion. As shown in the sequence of FIGS. 11, 12 and 13, when the weakening portion of the membrane 15 or collapsible septum collapses due to the effect induced by the screwing of the stopper 1 on the body of the container 30, the membrane gradually bends in correspondence of one of its portions of joint with the shoulder 15s, in the direction indicated by the arrow P; as the insertion of the rod 40 progresses, the membrane passes from a configuration substantially orthogonal to the axis X, through a configuration inclined with respect to the axis X, to a configuration in which it is substantially parallel to the axis X and is trapped between the lateral surface of the opening and the rod 40 itself. The presence of the shoulder 15s therefore makes it impossible for the membrane 15 or collapsible septum to collapse within the container 30 following its breaking, even if the portion near the shoulder 15s completely fails as a result of the bending. In a preferred, non-limiting embodiment, the membrane 15 or collapsible septum has a weakening portion, optionally located diametrically opposite to the joint portion with the shoulder 15s.

The second body 1b is schematically represented in FIG. 3 (lateral view) and in FIG. 4 (section view along the A-A lines of FIG. 3). The second body 1b acts as piston and contributes to determine in use a compression of the volume of the reservoir 20 retaining in particular the substance inside the recess itself, and forcing the leakage through the opening following the breaking of the membrane 15, or when present also of the auxiliary membrane 19.

The second body 1b comprises an upper portion 25, a lower portion 28, axially opposite to the upper portion 25 and an intermediate element 2 or sealing element, placed longitudinally between these two. The upper portion 25 has at least partially a substantially cylindrical shape with a first characteristic diameter and, in correspondence of an intermediate portion thereof, has a linear translation limiting element 2, which comprises a first upper shoulder 2s with a second characteristic diameter larger than the first one. In FIG. 4 the two characteristic diameters are indicated with $d_1$ and $d_2$ respectively. In other words, in the second body 1b there is an intermediate section between the lower portion and the upper portion, and this intermediate section comprises a linear translation limiting and sealing element, in particular a linear translation limiting element along the axis X.

In the embodiment represented in the attached figures, the upper portion 25 of the second body 1b comprises a plurality of ribs identified by the numerical reference 3, which depart radially from the aforementioned upper portion. These ribs are for example visible in FIG. 3, and as it is possible to observe in this figure they are preferably even if non-limiting thereto arranged in such a way to be oriented, for one of their directions of maximum extension, substantially parallel to the axis X. The set of ribs 3 at the point of maximum radial extension identifies a perimeter circumscribed by a circumference whose diameter is greater than the aforementioned first characteristic diameter $d_1$. The purpose of these ribs 3 is to optimize the alignment of the second body 1b with respect to the first body 1a with respect to the axis X and/or to contribute to reduce, ideally avoid, that the second body can oscillate with respect to the axis X of the stopper, positioning itself in such a way that one of its own axis is inclined with respect to the axis of the first body 1a. Thanks to this aspect, the sealing of the intermediate element or sealing element is optimized even when unintentional forces act on the second body 1b in a direction significantly inclined with respect to the axis X itself. The radially outermost portion of the ribs 3 is in substantial contact with the inner face of the lateral wall of the first body 1a.

The wall that departs from the shoulder determines an annular notch 2i substantially V-shaped, that is delimited inferiorly by a delimiting wall 2g which rejoins with the lower portion 28 cylindrical or slightly truncated cone of the second body 1b forming with it an acute angle. By observing the second body 1b frontally and in section along a plane parallel to the axis X, the delimiting wall 2g results to be inclined downwards, that is towards the bottom portion of the reservoir 20 that confines with the channel that allows the access to the membrane 15. In particular, by observing the delimiting wall 2g along a section on a plane parallel to the longitudinal axis X, this wall is oriented in inverted V with the vertex facing upwards. The Applicant observed that the downward inclination allows the sealing in case of pressure increases inside the reservoir 20. In fact, in case of pressure increase, the force exerted by the latter would tend to "open" the delimiting wall 2g, which however is laterally confined by the lateral wall. For this reason, an increasing friction force is created as the pressure inside the reservoir 20 increases. The delimiting wall, therefore, realizes a structure able to increase the pressure tightness and/or the contrast force against the inner surface of the lateral wall of the first body 1a according to the pressure increase inside the reservoir.

The Applicant observes that the maximum diameter of the lower portion 28 of the second body 1b is significantly smaller than the diameter identified by the lateral wall of the lower portion 20' of the upper cavity 1c of the first body 1a. The light (annular) that is present between the two elements allows the leakage of the substance beyond the undercut 17 in the shape of a swallow tail.

The delimiting wall 2g extends radially from the cylindrical portion of the second body 1b in such a way that its radially outermost portion presents a third characteristic diameter $d_3$ greater than the second characteristic diameter $d_2$; this third characteristic diameter $d_3$ is only slightly greater than the second characteristic diameter, being relatively greater in measure comprised between 1% and 2%.

The delimiting wall 2g, that extends for all the circumference of the corresponding portion of the second body 1b, defines a skirt that presents a relative elastic flexibility such as to be able to bend itself toward the lower cylindrical portion of the second body 1b in such a measure at least to allow the introduction of the second body within the first body 1a. In particular, the flexibility of the delimiting wall 2g must be such as to allow, with the above described bending, the third characteristic diameter $d_3$, which is substantially identified by it in rest condition, to be temporarily reduced by 10%-20%, for example, and preferably by 15%, without breaking and then return by elastic release substantially to the same third diameter $d_3$. Conveniently then at least this delimiting wall 2g is realized with an appropriate plastic material. However, the embodiment of the stopper here described is such that all the second body 1b is realized integrally in plastic material, for example for moulding. As in the case of the first body 1a, also the second body 1b is preferably realized in a plastic material resistant to acids and/or to corrosive substances, in particular those that can be contained inside the reservoir 20, and it is preferably even if non-limiting thereto a biocompatible material and i.e. of nature such as not to release substances when in contact with biological samples.

The delimiting wall 2g acts as a scraper able to exert a seal of liquid and powdered or granular substance, even during the linear translation action along the axis X that is determined during the movement of the second body 1b in compression. Thanks to this aspect, the confinement of the reservoir 20 suitable for containing the above-mentioned substance S occurs without the aid of any deformable sealing ring or O-ring, and this contributes to simplify the realization of the stopper object of the present disclosure, to reduce the separable components and to optimize the production economy especially on a large scale.

Therefore, the reservoir 20 within which the substance can be contained is defined between:
  the cylindrical annular portion defined between the outer face of the lateral wall of the second body 1b below the delimiting wall 2g, and the inner face of the upper portion 1r of the lateral wall of the first body 1a;
  (upper) the delimiting wall 2g;
  (through the annular light present between the lower portion 28 of the second body 1b and the lateral wall of the lower portion 20' of the upper cavity 1c of the first body 1a) the outer face of the lower portion 28 of the second body 1b and the inner face of the lateral wall delimiting the lower portion 20' of the above mentioned upper cavity 1c of the first body 1a;
  the second wall 13s;
  the opening portion and the corresponding membrane 15 or collapsible septum.

In other words the reservoir 20 presents a complex shape comprising an annular leakage portion that identifies an upper area and a lower area substantially joined each other, wherein the leakage portion is given by a dimensional difference, for example a difference in diameter, between a portion (in particular the lower portion) of the second body 1b when introduced in the upper cavity 1c of said first body 1a, and a portion of inner surface of a lateral wall of the first body 1a.

The radially outermost portion of the delimiting wall 2g can have a substantially sharp-edged shape, as in the case of FIG. 4a, or a rounded profile, as in the case of FIG. 4b. The Applicant found that the rounded profile contributes to improve the tightness of the delimiting wall 2g on the inner face of the lateral wall of the first body 1a, reduces scratches on the latter and improves the ease of mounting following the installation of the second body 1b within the first body 1a. The rounded profile also reduces the risk of plastic deformation of the edge portion of the delimiting wall 2g that might otherwise occur during the installation. Such rounding can be circular sector shaped or of other defined shape on a curve without angular points.

Unlike the delimiting wall 2g, the ring identified by the first upper shoulder 2s is not flexible and is advantageously configured to maintain the centring of the second body 1b within the cavity of the first body 1a.

As well visible in FIG. 4, the lower portion of the second body 1b presents a bell-shaped recess 5 given by the inner face of the lateral wall of the lower portion, which is inclined with respect to the axis X so that the mouth of the bell present in correspondence of the lower ending portion of the second body 1b has a greater diameter, sensibly maximum, and the head portion of the bell, recessed, has a smaller diameter with respect to the aforementioned maximum diameter.

The Applicant has conceived the shape of the bell 5 in a peculiar way, and this bell presents a shape that matches the shape that the reservoir 20 presents in its lower portion, and that in particular is given by the second wall 13s (in particular by its inner face) and by the opening that it identifies. Thanks to this aspect, when the second body 1b is introduced for maximum part inside the first body 1a, determining the aforesaid configuration of minimum axial extension, the lower annular perimeter 4f identified by the mouth of the bell 5 leans in the vertex of the notch that the second wall 13s identifies in the reservoir 20. For a careful measurements and design clearance, in this configuration, the surface of the bell identified by the inner face of the wall is at least partially and preferably substantially totally leaning on the inner face of the second wall 13s of the first body 1a, and at the same time, also the delimiting wall 2g is in substantially leaning in the undercut 17. This condition is represented in FIG. 15 and in FIG. 16. Thanks to this aspect, in the step of axial compression of the stopper there is a squeezing action of the substance contained in the reservoir 20, that allows to reduce to the minimum possible, ideally to zero, the quantity of substance that remains in the stopper 1 when this is in the configuration of minimum axial extension.

In correspondence of the head of the bell 5a housing 6 is obtained suitable for containing in use a portion of the end of the rod 40, in particular holding it by introduction by contrast; for this purpose the inner surface of the housing 6 is provided with a plurality of restraint ribs 7, preferably although non-limiting thereto arranged each one along a direction parallel to the direction identified by the axis X and extending towards the centre of the housing 6 itself, identified by the axis X. In this way, when the second body 1b is pushed within the first body 1a for a sufficient measure, the upper end portion of the rod 40 is introduced within the housing 6 and remains retained. Consequently, when the operator removes the stopper 1 from the container 30, he also holds the rod 40 together with the stopper itself, which at this point acts as a handle for the rod 40 which advantageously reduces the risk of contamination between the rod and the operator, and conveniently prevents the latter from contaminating himself, through portions of biological sample present on the rod and/or residues of substance.

In the attached figures, in particular in FIGS. 8, 10, 14 and 15, is represented a particular embodiment of the container 30 that is basically a tube for the collection and/or storage and/or analysis of biological samples, preferably realized in plastic material, for example and non-limiting thereto PP or PET or other plastic material, preferably designed in order to not to release substances to the biological sample when contained therein. In particular it can be a plastic test tube, optionally transparent, for example and non-limiting thereto to equal to 12 mm×80 mm. This shape is not to be understood as limiting. In the represented embodiment the container 30 presents a substantially cylindrical body open in correspondence of a single end (upper end) in correspondence of which is present the threading 34.

The Applicant observes that in substantial correspondence of the rupture of the membrane 15, the stopper 1 object of the present disclosure begins to screw on the container 30 in such a way that the threading—counter-threading coupling, together with the optional but preferable presence of a sealing ring 10k, guarantees a watertight coupling between the container 30 and the stopper 1, which prevents the exit of dust, liquids and gas from the container and the stopper. For this purpose, the threadings and counter-threadings described here are preferably of a double threading type. This allows a high feed rate along the axis X and reduces the weakening of the resistant section of the lateral wall that would otherwise be possible by using a single threading.

The Applicant observes that the threading—counter-threading coupling can be such that the threading 34 extends from the body of the container 30 or provides recesses realized on the body of the container 30. In particular, in the embodiments up to here described and represented in the attached figures, the threading 34 is present on the outer face of the lateral wall of the container 30 (the container can be said therefore with outer threading), and it extends radially from such outer face. This configuration is not to be understood as limiting, since—in a further embodiment—the threading of the container 30 can be positioned on the inner face of the lateral wall of the container 30, without this being understood as limiting. If the threading is present on the inner face of the lateral wall of the container 30, and therefore the container 30 is innerly threaded, there can be a solution in which the threading extends radially inwards, in particular to the centre of the container 30, or is realized through recesses on the inner face of the lateral wall of the container 30. Coherently, where the threading is made on the inner face of the lateral wall of the container 30, the counter-threading 10 present on the stopper 1 object of the present disclosure can be realized either on the outer face of the stopper 1 itself or, alternatively, on the annular wall 13v.

The opposite end (lower end) of the container 30 is marked by a V-shaped bottom portion 32, in which in particular the lateral wall progressively tapering towards the centre of the body of the container 30, which in the attached figures is centred on the axis X previously described. The bottom portion 32 is configured to exert a centring of the rod 40 and/or the swab 42 for the collection of biological samples along the axis X; therefore the V-shape of the bottom portion 32 cooperates with the guide portion 13s, 13v, and in particular with the second wall 13s, in order to contribute to the centring of the rod 40 along the axis X. Optionally, although non-limiting thereto, the V formed by the bottom portion 32 has no vertex, and the shape assumed by the bottom portion 32 is a truncated V-shape. In this case, the wall delimiting the bottom portion has a central section arranged on a plane orthogonal with respect to the plane of the axis X. On the bottom of the container 30, culture medium can be deposited in use.

One or more supporting feet 31, which realize a support skirt, can be present in the lower end of the container 30 in order to keep said container 30 in an upright position. The supporting feet 31 can be integral with the body of the container 30, for example in a moulding process, and can also be integral with the bottom portion 32 so that they can be joined together seamlessly. In addition, the supporting feet 31 can be realized from a ring joint with the lateral wall of the container 30.

The body of the stopper 1 is preferably realized of plastic material, resistant to acids and/or corrosive substances and/or is realized of biocompatible plastic material, so as not to release substances when in contact with biological samples. In a particular embodiment, the plastic material with which the stopper is realized is opaque, and therefore the substance S cannot be seen from the outside of the stopper itself. By hiding the substance S, and not allowing it to be freely transferred into the container 30, it is reduced the risk that certain subjects, comprising children, who potentially have access to the stopper 1 here described, swallow or otherwise enter into contact with the substance S. The use of an opaque stopper is also advantageous when the substance S contained in the reservoir 20 is photosensitive, because in this way the risk of degradation of the substance S itself is reduced, even when the stopper subject of the present disclosure must be left for a long time in areas exposed to light.

Although so far it has been described a releasing stopper 1 with threadings for coupling with the container 30, this specific technical characteristic is not intended to be restrictive; in fact, in an embodiment not shown in the attached figures, the removable coupling can be realized by clips, placed on the stopper 1 and suitable for engaging in undercuts present on the container 30 or, vice versa, by clips placed on the container 30 and suitable for engaging in undercuts present on the outer surface of the stopper 1. It is here observed that the clips can be configured to cause a significant compression of the stopper 1 against the container 30 during the closing, resulting in a reduction of the axial extension along the axis X of the assembly formed by the stopper 1 and the container 30, so as to indirectly allow the perforation of the membrane 15 through this compression or reduction of the axial extension.

During the mounting of the stopper 1, an operator, or even a machine, first performs the following steps:

a step of positioning of the substance within the first body 1a of the stopper 1 so that the substance is deposited in the reservoir 20 delimited by said membrane 15 or collapsible septum;

a subsequent step of positioning of the second body 1b at least partially within the first body 1a so that through said positioning a confinement of the reservoir 20 and of the substance within a closed volume, separated from the outer environment is determined.

The Applicant observes that at least the two above described steps can be realized through a machine for the assembly of stoppers 1; thanks to this aspect it is possible to mount a large quantity of stoppers 1 in a very short time. The stopper assembly here described can be alternatively carried out by the operator who carries out the following operations or it can be alternatively carried out by a specific operator of the stopper 1 manufacturing company.

In particular, the positioning of the substance S in the first body 1a can be a pouring of fluid, gelatinous material or solid material within the first body 1a, so that this fluid or solid material is first deposited over the membrane or collapsible septum and then fills part of the overlying portions of the cavity defined in the first body 1a. Also the positioning of the substance S in the first body 1a can comprise the introduction of two primary substances able to react to form a gas or vapor that can be trapped in the reservoir 20 thanks to the seal realized by the second body 1b. When the pouring is carried out by the aforesaid machine, this pouring can be carried out taking into account a predetermined pouring time (being known the flow of fluid or solid material from the machine to the stopper 1) or a difference in weight of fluid or solid material in a reservoir of the aforesaid machine, in order to have a predetermined and constant transfer of substance. In a particular embodiment the machine can comprise gripper elements to hold the first body 1a in a predetermined position and other elements to introduce the second body 1b at least partially within the first body 1a as above described.

When this successive step is carried out, and in particular when due to the introduction of the second body within the first body the volume of the reservoir 20 is properly defined and insulated, the stopper is ready to be operationally used.

In use through the element of sampling and storage of biological material the operator first takes the biological sample of interest and deposits it inside the container, taking care to position the element of sampling and storage of biological material in such a way that the swab 42 is positioned on the bottom of the container itself. When there is culture medium inside the container 30, the swab 42 can be conveniently placed in contact with the culture medium itself.

In a subsequent step of coupling, the stopper 1 is coupled with the container 30 and with the element for the collection and storage of biological material, and following the completion of the coupling, the container 30 has a closed and limited volume, in correspondence of one of its openings, by the presence of the stopper 1. As a result of the coupling of the stopper 1 with the container 30, in particular due to the interference with the rod 40 contained in the container 30, and through an axial compression between the stopper 1 and the container 30, a perforation of the membrane or collapsible septum such as to put in direct communication the inside of the container 30 with the reservoir 20 is determined. It is to be noticed that following the perforation of the membrane 15, the sealing action exerted by the delimiting wall 2g does not allow an overall release of the substance S within the container 30: although a leakage can be present even without pressure action towards the configuration of minimum axial extension, it is necessary in fact a further continuation of the application of the pressure force on the second body 1b in order to complete the release.

According to the specific embodiment of the element for the collection and storage of biological material, in particular in relation to the longitudinal development of the rod 40 compared to the longitudinal development of the container 30 into which the collection element is introduced, the perforation of the membrane 15 or collapsible septum takes place either before the contact between threading 34 and counter-threading 10, or downstream of such contact. In the first case, therefore, the step of coupling first determines a perforation or opening or fracture of the membrane 15 or collapsible septum and, following a relative sliding between the rod 40 and the stopper 1, in particular a relative sliding between the rod 40 and the first body 1a of the stopper 1, the coupling between the threading 34 and the counter-threading 10 is determined, and therefore the direct engagement between the stopper 1 and the container 30, following which the stopper 1 can actually be screwed on the container 30 definitively imprisoning the rod 40. There is therefore an engagement of the stopper 1 on the container 30 (therefore, a direct coupling) only after the perforation or opening or fracture of the membrane 15 or collapsible septum. The Applicant points out in particular that the perforation or opening or fracture of the membrane 15 or collapsible septum determines at least a partial, optionally a total, detachment of the membrane 15 or collapsible septum from the first body 1a, of which the closing element is an integral part (at least before the perforation or opening or fracture).

In the second case, the step of perforation or opening of the membrane 15 or collapsible septum occurs as a result of the engagement between the threading 34 and the counter-threading 10. In this case, the removable coupling comprises a progressive screwing of the stopper in particular of the first body 1a of the stopper 1 on the container 30, and the perforation of the membrane 15 or collapsible septum occurs through the progressive screwing of the stopper 1 on the container 30.

In order to release the substance S inside the volume of the container 30, the operator operates on the second body through the exercise of an action of pressure following or in concomitance of which an axial compression of the stopper 1 is determined that determines the progressive introduction of the second body 1b within the first body 1a. The progressive introduction of the second body 1b within the first body 1a, with an axial sliding along the axis X, determines a corresponding progressive reduction of the volume of the reservoir 20 and a progressive distribution of the substance within the container 30, which ends when the configuration of minimum axial extension is reached; in this configuration the reservoir 20 is substantially emptied and all the substance S is substantially in the container 30.

The progressive axial compression of the stopper 1 determines a sliding of the delimiting wall 2g (or at least a part of it, or a radially outermost or end portion) on the inner face of the side wall of the first body 1a in a direction substantially identified by the longitudinal axis X of the stopper. The sliding determines a sliding friction between the radially outermost or end portion of the delimiting wall 2g and the inner face previously mentioned, and thanks to this friction, and also thanks to the low roughness of the inner face, it is determined a seal of liquid and/or gas and/or powdered material such as to force the leakage of the substance S only from the open channel through the breaking of the membrane 15 or collapsible septum. There is therefore an elastic deformation of at least part of the delimiting wall 2g, following which a radially outer portion of said delimiting wall 2g exerts against the inner face of the lateral wall of the first body 1a a force oriented substantially in orthogonal direction with respect to the direction of advancement of the second body 1b within the first body 1a induced by the axial compression itself or, equivalently, a force oriented in substantially orthogonal direction to the longitudinal axis X of the stopper. It is observed that for keeping the seal towards the outer environment, i.e. for limiting the volume of the reservoir 20, there is no seal ring in rubbery or silicone material. Advantageously, the absence of components in silicone material and/or rubber, allows to reduce the risk of interaction and/or incompatibility with the substance contained in the reservoir 20, because the entire body of the stopper 1 is made of a single plastic material; this also allows to make the stopper 1 here described flexible in use with various types of substances, because the comparison towards possible interactions must be made only between the substance S and the specific type of plastic material used. Furthermore, the absence of components such as sealing rings or similar elements made of silicone material reduces the risk of cracking, which allows to keep a long-term storage. The absence of sealing rings or similar elements made of silicone material also helps to contain the production cost of the stopper here described.

The end portion 41 therefore introduces at least partially inside the first body 1a and causes a retaining of the membrane 15 or collapsible septum within the first body 1a, in particular by trapping the membrane 15 between itself, the lateral surface of an expulsion channel of the substance and the shoulder 15s positioned in substantial correspondence of said expulsion channel.

The coupling between the stopper 1 and the container 30 is such that the introduction of the end portion 41 within the first body 1a and within the reservoir 20 is sufficient to guarantee the engagement within the housing 6 obtained at the end of the bell 5; in substantial proximity of the configuration of minimum axial extension therefore the end portion 41 enters for introduction by contrast within the housing 6, and thanks to the action of the ribs 7 it remains retained there.

Preferably, in correspondence of the configuration of minimum axial extension, the second body 1b results in a blocking position in relation to the first body 1a such as axial extensions of the stopper 1 result operationally impossible; in other words, the blocking position is determined by an engagement of a stopping ring 28s of the second body 1b in correspondence of the present annular recess in correspondence of the inner face of the lateral wall of the first body 1a.

Therefore, a condition of double and/or simultaneous locking of the end portion 41 of the rod 40 and of the second body 1b with respect to the first body 1a occurs.

The Applicant notes that if a reagent substance is introduced into the body of the container 30, the release of the substance S from the reservoir 20 into the container 30 can trigger a chemical reaction. Consequently, it is noted that the separation of two chemicals reagent between each other, by the stopper 1 here described, allows the operator to start the chemical reaction only when desired and in complete safety, since the stopper 1 is firmly screwed onto the body of the container 30.

The Applicant observes that the characteristic perforation function of the membrane 15 or collapsible septum through the rod 40 when the perforation or opening element, in particular the swab for the collection of biological and/or microbiological material here described is introduced into the container 30, can be applied not only to stoppers 1 marked by the presence of the second body 1b as previously described, but also to stoppers which, according to the embodiment below described, comprise:
- a first body 1a configured to be directly coupled with the container 30 and comprising a coupling element 10 suitable for allowing the removable fixing of the stopper 1 in correspondence of an opening of the container 30 defining a first mounting configuration of the stopper on the container where, preferably, the stopper closes the container 30;
- a closing element (in particular the membrane 15 or collapsible septum), constituting at least a portion of the reservoir wall 20 and facing the inside of the container 30 in the mounting configuration, the closing element (in particular the membrane 15 or collapsible septum) being configured to be selectively openable and/or breakable, defining at least a second open configuration of the stopper, through the action of a perforation or opening element 40, 41, 42 distinct from stopper 1 and housed inside the container, to put the reservoir 20 in communication with the inside of the container.

In particular, the method of perforation of the membrane 15 or collapsible septum through the aforementioned rod 40, can also be applied to stoppers that, in combination with the characteristics here above expressed comprises a closing indicator 10k, suitable for engaging on or in correspondence of a closing counter-indicator 30k positioned on the container 30 determining a closing configuration of the container 30.

In this way the method comprises:
- a step of introduction of the perforation or opening element 40, 41, 42 inside the container 30 by an opening of the container itself, wherein said opening is suitable for housing the releasing stopper 1, so that this perforation or opening element 40, 41, 42 is removable from the container 30 and/or at least partially movable inside the container 30,
- a step of positioning of the releasing stopper 1 in substantial correspondence of the opening of the container 30.

Following the positioning step the closing element (in particular the membrane 15 or collapsible septum) is opened and/or fractured and/or broken by the perforation or opening element 40, 41, 42 allowing the release at least partial release of a predefined quantity of a substance S contained inside the reservoir S inside the container 30 through the exercise of a force between the releasing stopper 1 and the container 30.

In a non-limiting embodiment, the rod 40 can be provided with a body at least partially hollow and configured to allow the passage of the substance S from the reservoir 20 to the swab 42, in particular to allow the passage of the substance S from the reservoir 20 to a position in substantial correspondence or proximity of the swab 42. In this way the substance, in particular the fluid, passes between a cavity 41i inside the rod 40 and a surface outside the rod 40.

Therefore, an embodiment of the element for the collection of biological and/or microbiological material comprises a rod 40 comprising a cavity 41i having substantially axial development that is in communication with at least one first opening, in particular a first transfer duct 40k, preferably a first set of transfer ducts 40k and at least a second opening, in particular a second transfer duct 40f, preferably a second set of transfer ducts 40f.

In a particular embodiment, the cavity 41i therefore extends at least between the first height (or equivalently, the first portion of the rod 40) at which the first transfer duct 40k is present, or where present, the first set of transfer ducts 40k, and the second height (or second portion of the rod 40) at which the second transfer duct is present, or where present, the second set of transfer ducts 40f. In the embodiments shown in the attached figures, the first height or first portion substantially corresponds to the end portion of the rod 40, identified by the reference number 41, which is substantially opposite to the portion of the rod 40 in correspondence of which the swab 42 is present.

The first transfer duct 40k, or if present the first set of transfer ducts 40k, is preferably arranged in substantial correspondence of the first end portion of the rod 40, in particular being arranged at such a height that, when the rod 40 is introduced within the reservoir 20, this first transfer duct 40k, or if present the first set of transfer ducts 40k, allows the passage of the substance S within the cavity 41i.

Figure 18:
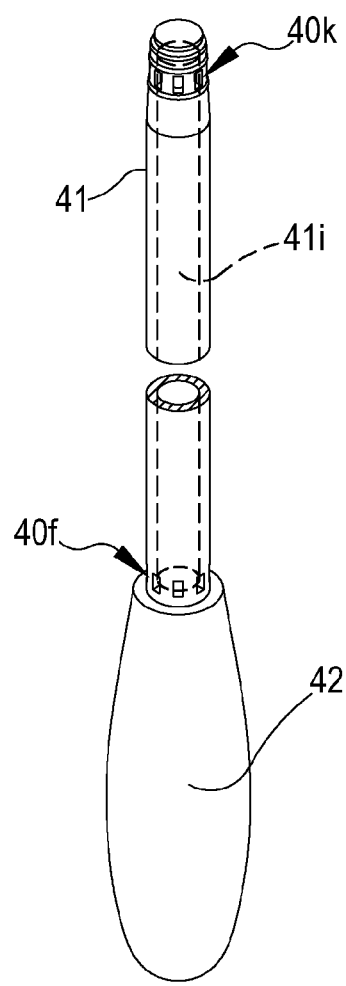
FIG. 18, FIG. 19 and FIG. 20 show an embodiment of a rod object of the present disclosure.

In the embodiment shown in FIG. 18, the first set of transfer ducts 40k extends radially over the perimeter of the lateral surface area of the rod 40, and the second set of transfer ducts 40f extends radially over the perimeter of the lateral surface area of the rod 40. This embodiment allows for example and non-limiting thereto the substance to be dispersed through the second set of transfer ducts 40f evenly over the swab 42, providing a uniform soaking and reducing the risk that sectors of the swab 42 can be poorly soaked with substance.

In particular, the second set of transfer ducts 40f allows the substance contained in the reservoir 20 to flow at a slightly higher height and in substantial contact with the swab 42. Preferably, in the embodiment shown in FIG. 19, the swab 42 is a flocked swab and is arranged around a portion of the rod 40 without cavities 41i that is introduced into it.

Figure 19:
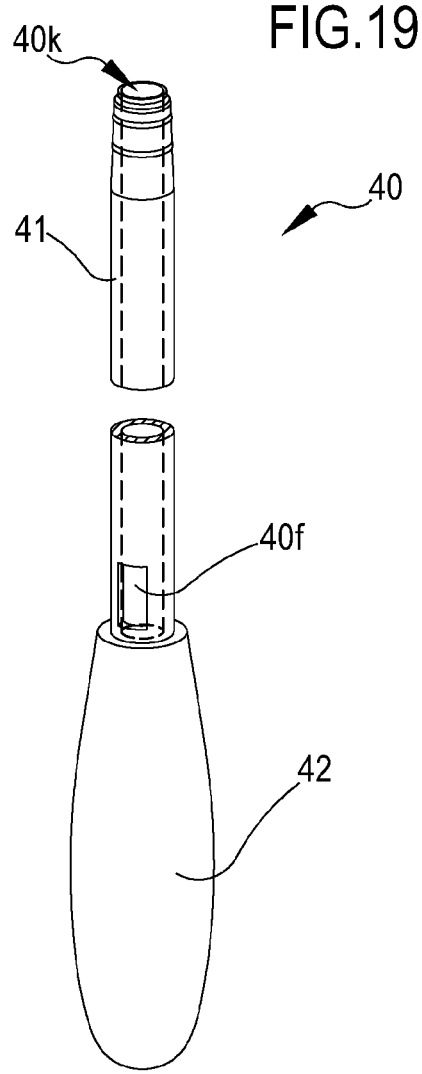

Alternatively, in an embodiment shown in FIG. 19, the first transfer duct 40k is an axial opening, in particular a coaxial head opening with cavity 41i, realized at the end of the rod 40. Although FIG. 19 shows a solution with a single second transfer duct 40f, this solution can be combined with the presence of a second transfer duct or a plurality of transfer ducts, in any of the embodiments above described.

Figure 20:
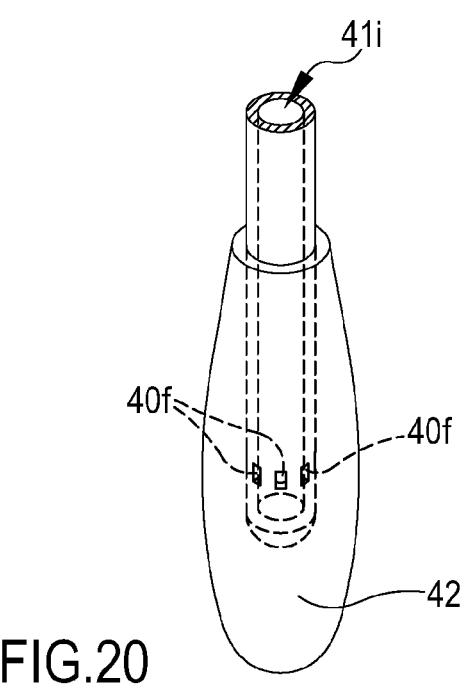

In a further embodiment, shown in FIG. 20, the second transfer duct 40f, or—where present—the second set of transfer ducts 40f, is arranged at a height at which the swab 42 is present. The second transfer duct 40f, or the second set of transfer ducts 40f, is therefore overhung and/or surrounded by the swab 42; with this embodiment it is therefore possible to carry out a transfer from the reservoir and a direct soaking of the swab 42 by a radially more inner portion. The embodiment here described can be combined with a first transfer duct 40k or a first set of transfer ducts 40k according to any of the embodiments here described.

When there is a first and/or second set of transfer ducts 40k, 40f, the plurality of transfer ducts belonging to the same set can be arranged on the same or different heights. In particular, the plurality of transfer ducts can be arranged in axial alignment along the direction of maximum extension of the inner cavity 41i (or, equivalently, the body of the rod).

The hollow rod, in the embodiments here described, can be coupled to a releasing stopper provided with first and second body reciprocally movable, in particular being able to be coupled to a releasing stopper, such as the one object of the present disclosure, or it can also be coupled to a traditional releasing stopper provided with reservoir and septum or membrane breakable for the release of the substance contained therein, as for example the one briefly described above.

The concepts herein are not limited to the embodiments shown in the drawings. For this reason, it is understood that where characteristics mentioned in the claims are followed by reference signs, these reference signs are included for the sole purpose of increasing the intelligibility of the claims, not constituting in any way a limitation of the claims themselves.

Finally, it is clear that additions, modifications or variants obvious for an expert in the art can be applied to the object of the present disclosure without thereby exceeding the scope of protection provided by the attached claims.

The invention claimed is:

1. A releasing stopper, suitable for and/or intended to be removably coupled with a container and configured to contain and selectively release a substance in the container, the stopper comprising:
    a first body configured to be directly coupled with the container and comprising a coupling element suitable for allowing the removable fastening of the releasing stopper in correspondence of an opening of the container defining a first mounting configuration of the releasing stopper on the container wherein, preferably, the releasing stopper closes the container;
    a second body, coupled and movable with respect to the first body and defining with the first body at least one reservoir configured to contain the substance, the reservoir being insulated from the outer environment in at least a first closed configuration of the releasing stopper, wherein the reservoir, at least in said first closed configuration of the releasing stopper, progressively reduces its volume as a result of a movement of the second body with respect to the first body,
    a closing element, positioned on the first body and constituting at least a portion of a wall of the reservoir and facing the inside of the container in the mounting configuration, the closing element being configured to be selectively openable and/or breakable, defining at least a second open configuration of the releasing stopper, through the action of a perforation or opening element different from the releasing stopper and housed within the container, to make the reservoir be in communication with the inside of the container;
    the second body comprising a cavity configured to allow the removable engagement of an ending portion of the perforation or opening element;
    wherein, in said at least a first closed configuration of the releasing stopper in which said reservoir is insulated from the outer environment, the second body cooperatively interacts with the first body for defining, with said first body, said at least one reservoir configured to contain the substance insulated from the outer environment.

2. The releasing stopper according to claim 1, wherein the second body is axially and translably movable with respect to the first body along a predefined axis of the releasing stopper and/or wherein at least a lower portion of the second body is movably housed inside the first body, to define the reservoir and/or wherein the reservoir is confined between the first body, in particular at least by a lateral wall of the first body, and the second body, in particular a lower portion of the second body, more in particular being centrally limited by the lower portion of the first body.

3. The releasing stopper according to claim 2, comprising a tapered portion or element, optionally positioned on the first body suitable for facilitating the targeting and/or driving of at least part of the perforation element towards the closing element, wherein the tapered portion is positioned in a position which is longitudinally outer with respect to the closing element and/or faces toward the closing element and/or wherein the tapered portion or element is integral to the first body and is substantially funnel-shaped, and is configured to be accessible from the inside of the container and/or wherein the closing element is configured to be selectively openable and/or breakable, defining at least the second open configuration of the releasing stopper, through the action of a perforation or opening element different from the releasing stopper and different from the container and/or movably, optionally removably, housed inside the container.

4. The releasing stopper according to claim 1, wherein said cavity is configured to allow the removable engagement of said ending portion of the perforation or opening element through introduction by contrast; the releasing stopper being configured to allow the introduction by contrast only when in open configuration, in particular in substantial proximity or correspondence of a configuration of minimum axial extension of the releasing stopper.

5. The releasing stopper according to claim 1, suitable for and/or intended to be removably coupled against a head portion of the container, and/or wherein the first body is configured and intended to be removably coupled against a head portion of the container, in particular wherein the first body is configured for being rigidly united and/or fixed on a head portion of the container and/or is configured for striking against a head portion of the container.

6. The releasing stopper according to claim 1, wherein, at least when the releasing stopper is in the first closed configuration, the closing element is integral to the first body; and/or wherein the closing element is a waterproof element, configured and specifically designed to retain solids, in particular powders, liquids and/or gases.

7. The releasing stopper according to claim 1, wherein:
    the closing element is a membrane or collapsible septum, optionally provided with a weakening portion; and/or wherein the closing element is configured to withstand the pressure induced on the reservoir by an axial compression of the second body with respect to the first body, optionally manually induced by an operator; the closing element comprising a weakening portion suitable to break first by mechanical contrast induced by the perforation or opening element, and/or wherein in the open configuration the substance is at least partially released into the container and/or wherein the releasing stopper is configured to release the substance into the container when in the open configuration, in particular by keeping, when coupled to the container, an insulation of the volume overall identified by the container-reservoir assembly insulated from the outer environment and/or in particular by causing an exclusive release of the substance through the opening identified by the breaking of the closing element.

8. The releasing stopper according to claim 1, comprising a retaining element of the closing element, configured to prevent the release and/or fall of the closing element within the container; the retaining element being in particular configured to retain the closing element inside the first body;

the retaining element comprising a shoulder against which the closing element rests or folds when in contrast with the perforation or opening element, the shoulder being positioned in substantial correspondence of a channel between the reservoir and the closing element.

9. The releasing stopper according to claim 8, wherein in the open operating configuration, the closing element is retained by the shoulder and is trapped between the channel and part of the perforation or opening element positioned within the channel, and wherein the closing element is configured to break without releasing splinters or portions.

10. The releasing stopper according to claim 1, wherein:

the second body is movable with respect to the first body and defines through its axial movement at least a configuration of maximum axial extension of the releasing stopper along a longitudinal axis and a configuration of minimum axial extension of the releasing stopper along the longitudinal axis;

the first closed configuration comprises the configuration of maximum axial extension of the releasing stopper and the second open configuration comprises the configuration minimum axial extension of the releasing stopper;

the second open configuration takes place in correspondence of a longitudinal extension, optionally substantially intermediate, between the longitudinal extension corresponding to the configuration of maximum axial extension of the releasing stopper and the longitudinal extension corresponding to the configuration of minimum axial extension of the releasing stopper.

11. The releasing stopper according to claim 1, wherein the first body comprises an upper cavity, laterally delimited by a lateral wall, and a lower cavity separated each other by the presence of the closing element, and wherein the second body is configured to be installed in correspondence of the upper cavity of the first body.

12. The releasing stopper according to claim 1, wherein:

the second body comprises an intermediate section comprising a sealing and linear translation limitation element, configured to determine a confinement of the reservoir volume and to limit the stroke of the second body with respect to the first body between the configuration of maximum linear extension and the configuration of minimum linear extension of the releasing stopper, wherein the second body comprises an upper portion and a lower portion with respect to which the intermediate section is longitudinally interposed, wherein the diameter substantially identified by the radially outermost section of the sealing element is significantly greater than the diameter identified by the upper portion and/or the lower portion of the second body, wherein the sealing element comprises, optionally at a first upper height, a shoulder configured to engage in use with a retention portion prominent from the inner face of the lateral wall of the first body, the engagement between the retention portion and the shoulder being such as to determine the impossibility of complete extraction of the second body from the first body when the latter has been previously inserted, and/or wherein the sealing element comprises a delimiting walls specifically configured to determine the sealing and confinement of the reservoir volume, the delimiting wall having a conformation such as to also determine the limitation of the translation of the second body with respect to the first body in the configuration of minimum axial extension.

13. The releasing stopper according to claim 1, wherein the first body comprises an annular recess, optionally positioned at a substantially intermediate height between a minimum and a maximum height defined by the first body and/or positioned at a height substantially corresponding to the height at which the closing element is located; the annular recess being configured to speed up the cooling of the first body, in particular of the portion of the first body in correspondence of which it is positioned with respect to ending portions of the first body.

14. The releasing stopper according to claim 10, wherein the first body comprises a pressure release element, configured to allow the evacuation of a predefined volume of air when the second body is introduced into the first body, and wherein the pressure release element is configured to allow the evacuation of a predefined volume of air when the second body is introduced into the first body in a non-operational mounting configuration of the second body into the first body, without affecting the tightness of the reservoir itself when at least the maximum axial extension configuration is reached, optionally wherein the pressure release element comprises a notch positioned in correspondence of a head portion of the inner face of the lateral wall of the first body and/or positioned in correspondence of a head portion of the upper cavity.

15. The releasing stopper according to claim 1, wherein the second body has a recess, optionally bell-shaped, configured to be coupled with a bottom portion of the reservoir and having a shape substantially following the shape identified by the bottom of the reservoir, optionally wherein the recess opens on the cavity, the cavity having a plurality of restraint ribs of the perforation or opening element.

16. A releasing stopper, suitable for and/or intended to be removably coupled with a container and configured to contain and selectively release a substance in the container, the stopper comprising:

a first body configured to be directly coupled with the container and comprising a coupling element suitable for allowing the removable fastening of the releasing stopper in correspondence of an opening of the container defining a first mounting configuration of the releasing stopper on the container wherein, preferably, the releasing stopper closes the container;

a second body, coupled and movable with respect to the first body and defining with the first body at least one reservoir configured to contain the substance, the reservoir being insulated from the outer environment in at least a first closed configuration of the releasing stopper, the first body comprising a closing element, constituting at least a portion of a wall of the reservoir and facing the inside of the container in the mounting configuration, the closing element being configured to be selectively openable and/or breakable, defining at least a second open configuration of the releasing stopper, through the action of a perforation or opening element different from the releasing stopper and housed within the container, to make the reservoir be in communication with the inside of the container;

the second body comprising a cavity configured to allow the removable engagement of an ending portion of the perforation or opening element;

wherein, in said at least a first closed configuration of the releasing stopper in which said reservoir is insulated from the outer environment, the second body cooperatively interacts with the first body for defining, with said first body, said at least one reservoir configured to contain the substance insulated from the outer environment;

said first body comprising a fall-preventing retaining element of the closing element, configured to prevent a fall of the closing element.

17. A kit comprising:

a container for the storage of a biological sample, the container comprising a body openable at least in correspondence of at least one own first portion;

a perforation or opening element different from, and removably engageable to, the releasing stopper and removably housed within the container;

a releasing stopper, suitable for and/or intended to be removably coupled with said container and configured to contain and selectively release a substance in the container, wherein the releasing stopper comprises:

a first body configured to be directly coupled with the container and comprising a coupling element suitable for allowing the removable fastening of the releasing stopper in correspondence of an opening of the container defining a first mounting configuration of the releasing stopper on the container wherein, preferably, the releasing stopper closes the container;

a second body, coupled and movable with respect to the first body and defining with the first body at least one reservoir configured to contain the substance, the reservoir being insulated from the outer environment in at least a first closed configuration of the releasing stopper, a closing element, constituting at least a portion of a wall of the reservoir and facing the inside of the container in the mounting configuration, the closing element being configured to be selectively openable and/or breakable, defining at least a second open configuration of the releasing stopper, through the action of said perforation or opening element, to make the reservoir be in communication with the inside of the container;

the second body comprising a cavity configured to allow the removable engagement of an ending portion of the perforation or opening element;

wherein, in said at least a first closed configuration of the releasing stopper in which said reservoir is insulated from the outer environment, the second body cooperatively interacts with the first body for defining, with said first body, said at least one reservoir configured to contain the substance insulated from the outer environment.

* * * * *